US010507232B2

(12) United States Patent
Bloom et al.

(10) Patent No.: US 10,507,232 B2
(45) Date of Patent: Dec. 17, 2019

(54) MATERIALS AND METHODS FOR THE TREATMENT OF LATENT VIRAL INFECTION

(71) Applicants: UNIVERSITY OF FLORIDA RESEARCH FOUNDATION, INCORPORATED, Gainesville, FL (US); DUKE UNIVERSITY, Durham, NC (US)

(72) Inventors: David C. Bloom, Gainesville, FL (US); Dane M. Phelan, Gainesville, FL (US); Bryan R. Cullen, Durham, NC (US); Matthew E. Kennedy, Chapel Hill, NC (US)

(73) Assignees: University of Florida Research Foundation, Incorporated, Gainesville, FL (US); Duke University, Durham, NC (US)

(*) Notice: Subject to any disclaimer, the term of this patent is extended or adjusted under 35 U.S.C. 154(b) by 189 days.

(21) Appl. No.: 15/300,807

(22) PCT Filed: Apr. 2, 2015

(86) PCT No.: PCT/US2015/024094
§ 371 (c)(1),
(2) Date: Sep. 30, 2016

(87) PCT Pub. No.: WO2015/153889
PCT Pub. Date: Oct. 8, 2015

(65) Prior Publication Data
US 2017/0020994 A1 Jan. 26, 2017

Related U.S. Application Data

(60) Provisional application No. 61/973,995, filed on Apr. 2, 2014.

(51) Int. Cl.
*A61K 38/46* (2006.01)
*C12N 9/22* (2006.01)
*A61K 31/52* (2006.01)
*C12N 7/00* (2006.01)
*A61K 45/06* (2006.01)
*A61K 31/045* (2006.01)
*A61K 31/522* (2006.01)
*A61K 31/7072* (2006.01)
*A61K 48/00* (2006.01)

(52) U.S. Cl.
CPC .......... *A61K 38/465* (2013.01); *A61K 31/045* (2013.01); *A61K 31/52* (2013.01); *A61K 31/522* (2013.01); *A61K 31/7072* (2013.01); *A61K 45/06* (2013.01); *C12N 7/00* (2013.01); *C12N 9/22* (2013.01); *C12Y 301/00* (2013.01); *A61K 48/00* (2013.01); *C07K 2319/80* (2013.01); *C12N 2710/16611* (2013.01); *C12N 2710/16661* (2013.01)

(58) Field of Classification Search
None
See application file for complete search history.

(56) References Cited

U.S. PATENT DOCUMENTS

| 6,140,081 | A | 10/2000 | Barbas |
| 6,453,242 | B1 | 9/2002 | Eisenberg et al. |
| 6,534,261 | B1 | 3/2003 | Cox, III et al. |
| 6,607,882 | B1 | 8/2003 | Cox, III et al. |
| 6,824,978 | B1 | 11/2004 | Cox, III et al. |
| 6,933,113 | B2 | 8/2005 | Case et al. |
| 6,979,539 | B2 | 12/2005 | Cox, III et al. |
| 7,013,219 | B2 | 3/2006 | Case et al. |
| 7,163,824 | B2 | 1/2007 | Cox, III et al. |
| 2005/0064474 | A1 | 3/2005 | Urnov et al. |
| 2007/0218528 | A1 | 9/2007 | Miller |
| 2008/0131962 | A1 | 6/2008 | Miller |
| 2011/0201055 | A1 | 8/2011 | Doyon et al. |
| 2011/0301073 | A1 | 12/2011 | Gregory et al. |
| 2013/0122581 | A1* | 5/2013 | Voytas ................ C12N 9/22 435/320.1 |
| 2013/0274129 | A1* | 10/2013 | Katzen ............ C12N 15/1093 506/9 |

FOREIGN PATENT DOCUMENTS

| WO | WO 98/53058 | 11/1998 |
| WO | WO 98/53059 | 11/1998 |
| WO | WO 98/53060 | 11/1998 |
| WO | WO 99/53043 | 10/1999 |
| WO | WO 95/32283 A1 | 11/1999 |
| WO | WO 02/16536 | 2/2002 |
| WO | WO 03/016496 | 2/2003 |
| WO | WO 2013/012674 | 1/2013 |
| WO | WO 2013/173129 | 11/2013 |
| WO | WO 2014/039585 A2 | 3/2014 |

OTHER PUBLICATIONS (Molecular Therapy, Feb. 2014 vol. 22, p. 303-311).*
Reddy et al. (World Journal of Gastroenterology, Dec. 2013, vol. 19, p. 9328-9333).*
Qi, L. S. et al. "Repurposing CRISPR as an RNA-Guided Platform for Sequence-Specific Control of Gene Expression" *Cell*, Feb. 28, 2013, pp. 1173-1183, vol. 152.
Written Opinion in International Application No. PCT/US15/24094, dated Oct. 8, 2015, pp. 1-10.
Invitation to Pay Additional Fees for Application No. PCT/US2015/024094 dated Aug. 3, 2015.
International Search Report for Application No. PCT/US2015/024094 dated Oct. 8, 2015.
International Preliminary Report on Patentability for Application No. PCT/US2015/024094 dated Oct. 13, 2016.

* cited by examiner

*Primary Examiner* — Agnieszka Boesen
(74) *Attorney, Agent, or Firm* — Wolf, Greenfield & Sacks, P.C.

(57) ABSTRACT

The subject invention pertains to materials and methods for the treatment of latent viral infections.

3 Claims, 14 Drawing Sheets
(3 of 14 Drawing Sheet(s) Filed in Color)
Specification includes a Sequence Listing.

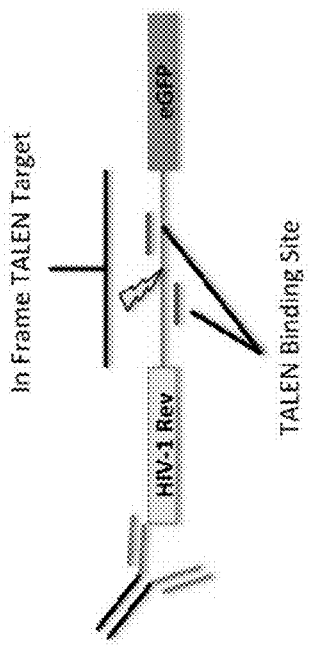
FIG. 2A
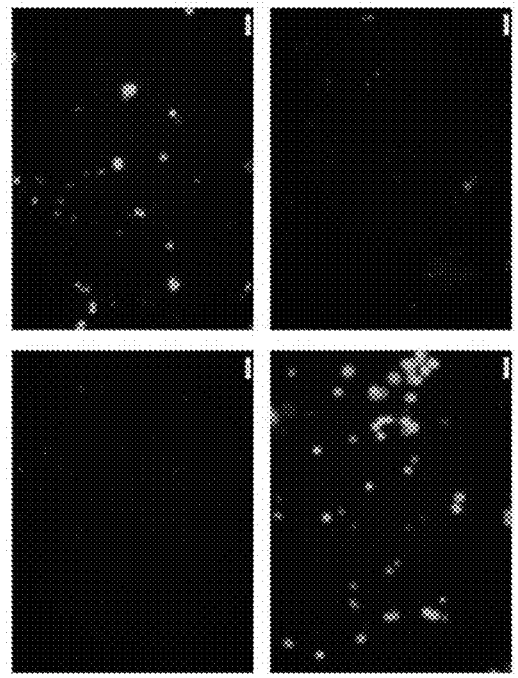
FIG. 2C
FIG. 2B

TALE-VP16 Binding Site

ICP0 Indicator            ICP4 Indicator

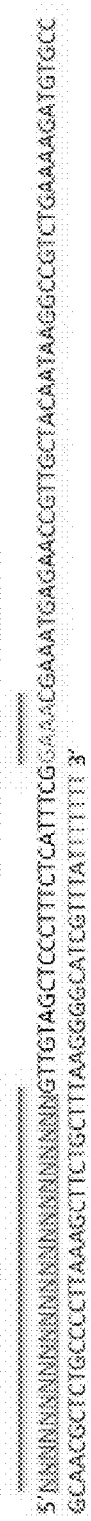
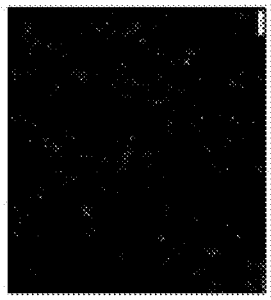
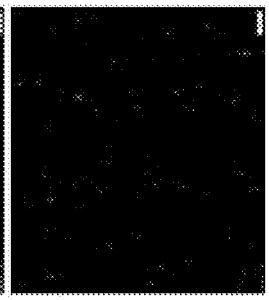
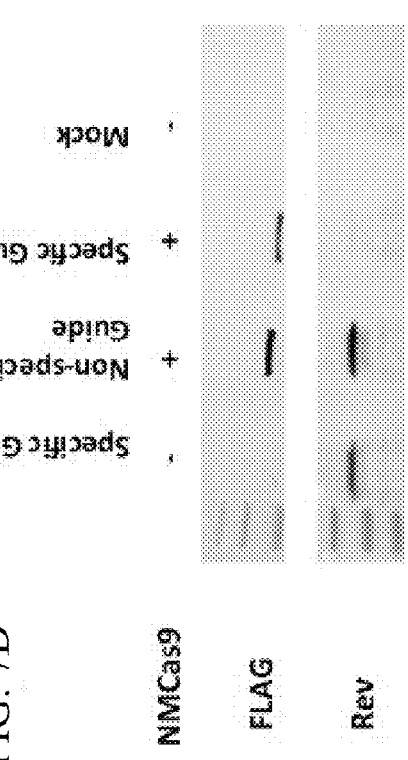
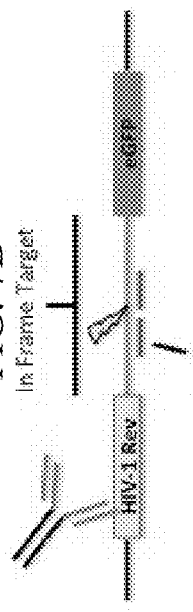
FIG. 7A
FIG. 7B
FIG. 7C
FIG. 7D

SEQUENCE LISTING

```
<160> NUMBER OF SEQ ID NOS: 30

<210> SEQ ID NO 1
<211> LENGTH: 3300
<212> TYPE: DNA
<213> ORGANISM: Neisseria meningitidis

<400> SEQUENCE: 1
atggattaca aagacgatga cgataagcca aagaagaagc ggaaggtcgg cggcgccgcc      60
ttcaaaccca acagcatcaa ctatatcctg ggactcgaca tcggcattgc ctccgtcgga     120
tgggccatgg tggagatcga cgaggaagag aacccatca gactcattga cctgggagtc     180
agggtgtttg agagggctga ggtccccaaa acaggcgatt ccctggctat ggctaggaga     240
ctggccagga gcgtgaggag gctcacaaga aggagggccc acaggctcct caggacaagg     300
```

```
aggctcctca agagggaagg cgtgctacag gctgccaact tcgatgagaa tggactcatc    360
aagtccctcc ccaataccccc ttggcaactg agagctgctg ctctcgacag aaaactgacc    420
cccctggaat ggagcgctgt cctcctccat ctgattaagc acaggggcta cctctcccag    480
aggaagaacg agggcgaaac cgccgacaag gaactcggag ccctcctcaa aggagtcgcc    540
ggaaatgccc acgccctaca gaccggagat ttcagaaccc ctgccgagct ggccctgaat    600
aagttcgaga aggagagcgg ccacattagg aaccagaggt ccgactactc ccacacattt    660
tccaggaagg acctccaggc tgagctgatc ctgctgttcg agaagcagaa ggagttcggc    720
aatccccacg tcagcggcgg cctcaaggaa ggaatcgaga cactgctcat gacccaaagg    780
cccgccctct ccggcgatgc tgtgcagaaa atgctcggcc attgcacctt tgaacctgct    840
gagcccaagg ccgctaagaa cacctacacc gccgagagat tcatttggct cacaaagctc    900
aacaatctca ggattctgga gcagggcagc gaaagacctc tcacagacac agagagggct    960
accctcatgg acgagcccta taggaagtcc aagctgacct acgctcaggc tagaaagctg   1020
ctgggcctgg aggacacagc cttcttcaaa ggcctgagat atggcaaaga caacgccgaa   1080
gcgagcaccc tgatggagat gaaagcctac cacgccatta gcagagctct ggagaaagaa   1140
ggcctgaagg acaaaaagag ccctctgaac ctctcccctg aactacagga cgagatcggc   1200
accgccttct ccctgtttaa aaccgatgag gacataaccg gaaggctgaa ggatagaata   1260
cagcccgaga ttctggaggc cctgctcaag cacatttcct tcgataagtt cgtccaaata   1320
agcctcaagg ccctcaggag aattgtccct ctgatggaac agggcaagag atacgacgag   1380
gcgtgcgccg agatttatgg cgaccattat ggcaaaaaaa acacagagga gaagatttat   1440
ctgcccccca tccccgctga cgagatcaga aaccctgtcg tcctcagggc cctgagccaa   1500
gccaggaagg tgatcaatgg agtggtgaga aggtacggct cccctgccag aatacacatc   1560
gaaacagcta gagaggtcgg aaaagagcttc aaggatagaa agaaattga aaaagacaa   1620 gaggaaaata ggaaagacag ggaaaaggcc gccgccaagt ttagggaata cttccctaat   1680
ttcgtgggcg agcccaaatc caaggacatt ctcaaactga ggctctatga gcagcagcat   1740
ggaaagtgcc tctacagcgg caaggaaatt aacctgggca ggctcaatga aagggatac   1800 gtcgaaatcg atcacgccct gcccttcagc aggacatggg acgatagctt taacaacaaa   1860
gtcctcgtgc tggaagcgga gaaccaaaac aagggaaacc agacccctta cgagtacttc   1920
aacggcaagg ataactccag agagtggcag gagtttaagg ccagggtgga gacctccagg   1980
ttccccagaa gcaagaagca gagaatactg ctccagaagt tgacgagga cggcttcaag   2040 gagaggaacc tcaacgatac caggtacgtg aacaggttcc tgtgccagtt tgtcgctgac   2100
aggatgagcc tcaccggaaa gggaaagaag agggtctttg cgagcaacgg ccagattacc   2160
aacctgctga gaggcttctg gggcctgaga aaggtcagag ctgagaacga cagacatcac   2220
gctctcgatg ctgtggtcgt ggcttgctcc accgtggcca tgcagcaaaa gatcacaagg   2280
ttcgtgaggt acaaggaaat gaacgccttc gacggcaaaa caatcgacaa ggagaccggc   2340
gaggtgctcc accagaaaac ccacttccct caaccttggg agttcttcgc ccaggaggtc   2400
atgatcaggt gtttggcaa gcccgacgga agcctgaat tgaggaggc cgataccctg   2460 gagaagctga ggacactcct cgctgaaaag ctgagctcca gacccgaagc cgtgcacgag   2520
tacgtcacac tctctgttcgt gtccagagct cccaatagga agatgtccgg acagggccac   2580
atggagaccg tcaaaagcgc taagaggctg gacgaaggcg tcagcgtcct gagggtcccct   2640 ctgacccaac tcaaactcaa ggacctggaa aagatggtga acagggagag agagcccaag   2700
```

```
ctctacgagg cccctcaaagc cagactcgaa gcccataagg atgatcccgc caaggcgttc    2760
gctgagccct tctacaaata cgacaaggcc ggaaacagaa cccaacaagt caaggccgtg    2820
agagtcgagc aagtccagaa accggagtc tgggtcagga accataacgg catcgctgac    2880
aatgccacca tggtcagagt ggatgtcttc gagaagggcg acaagtacta cctcgtccct    2940
atctacagct ggcaagtggc caagggaatc ctccctgata gggccgtcgt gcaaggaaag    3000
gacgaggaag actggcagct gattgacgac agcttcaatt ttaaattctc cctccaccct    3060
aacgatctgg tcgaggtgat taccaagaag gccagaatgt tcggatactt cgccagctgc    3120 catagggca caggcaacat taatatcagg atacacgacc tggaccacaa gatcggcaag    3180
aacggcatcc tggagggaat tggagtgaag accgctctga gcttccagaa gtaccagatt    3240
gacgagctcg gcaaggagat taggccttgt aggctgaaga gaggccccc cgtgagataa    3300
```

<210> SEQ ID NO 2
<211> LENGTH: 17
<212> TYPE: DNA
<213> ORGANISM: Artificial Sequence
<220> FEATURE:
<223> OTHER INFORMATION: Synthetic

<400> SEQUENCE: 2
gcgcaattgc atccagg                                                    17

<210> SEQ ID NO 3
<211> LENGTH: 17
<212> TYPE: DNA
<213> ORGANISM: Artificial Sequence
<220> FEATURE:
<223> OTHER INFORMATION: Synthetic

<400> SEQUENCE: 3
gcatgcaccg cttctgc                                                    17

<210> SEQ ID NO 4
<211> LENGTH: 20
<212> TYPE: DNA
<213> ORGANISM: Artificial Sequence
<220> FEATURE:
<223> OTHER INFORMATION: Synthetic

<400> SEQUENCE: 4
ggccgccacc ggccgtgacg                                                 20

<210> SEQ ID NO 5
<211> LENGTH: 20
<212> TYPE: DNA
<213> ORGANISM: Artificial Sequence
<220> FEATURE:
<223> OTHER INFORMATION: Synthetic

<400> SEQUENCE: 5
cgccgcgccc gccggcccag                                                 20

<210> SEQ ID NO 6
<211> LENGTH: 15
<212> TYPE: DNA
<213> ORGANISM: Artificial Sequence
<220> FEATURE:
<223> OTHER INFORMATION: Synthetic

<400> SEQUENCE: 6
gggacgcgcg gccat                                                      15

<210> SEQ ID NO 7
<211> LENGTH: 17
<212> TYPE: DNA
<213> ORGANISM: Artificial Sequence
<220> FEATURE:
<223> OTHER INFORMATION: Synthetic

<400> SEQUENCE: 7
ggcagatggc gcggatg                                                    17

<210> SEQ ID NO 8
<211> LENGTH: 24
<212> TYPE: DNA
<213> ORGANISM: Artificial Sequence
<220> FEATURE:
<223> OTHER INFORMATION: Synthetic

<400> SEQUENCE: 8
gcggtggccg gccgcgacgc cacg                                            24

<210> SEQ ID NO 9
<211> LENGTH: 32
<212> TYPE: DNA
<213> ORGANISM: Artificial Sequence
<220> FEATURE:
<223> OTHER INFORMATION: Synthetic

<400> SEQUENCE: 9
gcggtggccg gccgcgacgc cacgggccgc tt                                   32

<210> SEQ ID NO 10
<211> LENGTH: 24
<212> TYPE: DNA
<213> ORGANISM: Artificial Sequence
<220> FEATURE:
<223> OTHER INFORMATION: Synthetic

<400> SEQUENCE: 10
gccgcggccg gagggacccg cggg                                            24

<210> SEQ ID NO 11
<211> LENGTH: 32
<212> TYPE: DNA
<213> ORGANISM: Artificial Sequence
<220> FEATURE:
<223> OTHER INFORMATION: Synthetic

<400> SEQUENCE: 11
cccgcggccg gagggacccg cgggccccgc tt                                   32

<210> SEQ ID NO 12
<211> LENGTH: 24
<212> TYPE: DNA
<213> ORGANISM: Artificial Sequence
<220> FEATURE:
<223> OTHER INFORMATION: Synthetic

<400> SEQUENCE: 12 gggggggccct gccgccggcg ccgc                                           24

<210> SEQ ID NO 13
<211> LENGTH: 32
<212> TYPE: DNA
<213> ORGANISM: Artificial Sequence
<220> FEATURE:
<223> OTHER INFORMATION: Synthetic

<400> SEQUENCE: 13
cgggggccct gccgccggcg ccgcccggga tt                32

<210> SEQ ID NO 14
<211> LENGTH: 24
<212> TYPE: DNA
<213> ORGANISM: Artificial Sequence
<220> FEATURE:
<223> OTHER INFORMATION: Synthetic

<400> SEQUENCE: 14
ggggtcaggt accgcggggc gaac                24

<210> SEQ ID NO 15
<211> LENGTH: 32
<212> TYPE: DNA
<213> ORGANISM: Artificial Sequence
<220> FEATURE:
<223> OTHER INFORMATION: Synthetic

<400> SEQUENCE: 15
agggtcaggt accgcggggc gaaccgctga tt                32

<210> SEQ ID NO 16
<211> LENGTH: 24
<212> TYPE: DNA
<213> ORGANISM: Artificial Sequence
<220> FEATURE:
<223> OTHER INFORMATION: Synthetic

<400> SEQUENCE: 16
ggcgtcacgc ccactatcag gtac                24

<210> SEQ ID NO 17
<211> LENGTH: 32
<212> TYPE: DNA
<213> ORGANISM: Artificial Sequence
<220> FEATURE:
<223> OTHER INFORMATION: Synthetic

<400> SEQUENCE: 17
ggcgtcacgc ccactatcag gtacaccagc tt                32

<210> SEQ ID NO 18
<211> LENGTH: 278
<212> TYPE: DNA
<213> ORGANISM: Gallus gallus

<400> SEQUENCE: 18
tcgaggtgag ccccacgttc tgcttcactc tccccatctc cccccctcc ccaccccaa                60 ttttgtattt atttattttt taattatttt gtgcagcgat gggggcgggg ggggggggg                120 ggcgcgcgcc aggcggggcg gggcggggcg aggggcgggg cggggcgagg cggagaggtg                180
cggcggcagc caatcagagc ggcgcgctcc gaaagtttcc ttttatggcg aggcggcggc                240
ggcggcggcc ctataaaaag cgaagcgcgc ggcgggcg                278

<210> SEQ ID NO 19
<211> LENGTH: 34
<212> TYPE: PRT
<213> ORGANISM: Artificial Sequence
<220> FEATURE:
<223> OTHER INFORMATION: Synthetic

<400> SEQUENCE: 19

Asn Asn His Asp Asn Asn His Asp Asn Ile Asn Ile Asn Gly Asn Gly
1               5                   10                  15

Asn Asn His Asp Asn Ile Asn Gly His Asp His Asp Asn Ile Asn Asn
            20                  25                  30

Asn Asn

<210> SEQ ID NO 20
<211> LENGTH: 34
<212> TYPE: PRT
<213> ORGANISM: Artificial Sequence
<220> FEATURE:
<223> OTHER INFORMATION: Synthetic

<400> SEQUENCE: 20

Asn Asn His Asp Asn Ile Asn Gly Asn Asn His Asp Asn Ile His Asp
1               5                   10                  15

His Asp Asn Asn His Asp Asn Gly Asn Gly His Asp Asn Gly Asn Asn
            20                  25                  30

His Asp

<210> SEQ ID NO 21
<211> LENGTH: 40
<212> TYPE: PRT
<213> ORGANISM: Artificial Sequence
<220> FEATURE:
<223> OTHER INFORMATION: Synthetic

<400> SEQUENCE: 21

Asn Asn Asn Asn His Asp His Asp Asn His His Asp His Asp Asn Ile
1               5                   10                  15

His Asp His Asp Asn His Asn His His Asp His Asp Asn His Asn Gly
            20                  25                  30

Asn His Asn Ile His Asp Asn Asn
        35                  40

<210> SEQ ID NO 22
<211> LENGTH: 40
<212> TYPE: PRT
<213> ORGANISM: Artificial Sequence
<220> FEATURE:
<223> OTHER INFORMATION: Synthetic

<400> SEQUENCE: 22

His Asp Asn Asn His Asp His Asp Asn His His Asp Asn His His Asp
1               5                   10                  15

His Asp His Asp Asn His His Asp His Asp Asn His Asn His His Asp
            20                  25                  30

His Asp His Asp Asn Ile Asn Asn
        35                  40

<210> SEQ ID NO 23
<211> LENGTH: 30
<212> TYPE: PRT
<213> ORGANISM: Artificial Sequence
<220> FEATURE:
<223> OTHER INFORMATION: Synthetic

```
<400> SEQUENCE: 23

Asn Asn Asn Asn Asn Asn Asn Ile His Asp Asn Asn His Asp Asn Asn
1               5                   10                  15

His Asp Asn Asn Asn Asn His Asp His Asp Asn Ile Asn Gly
            20                  25                  30

<210> SEQ ID NO 24
<211> LENGTH: 34
<212> TYPE: PRT
<213> ORGANISM: Artificial Sequence
<220> FEATURE:
<223> OTHER INFORMATION: Synthetic

<400> SEQUENCE: 24

Asn Asn Asn Asn His Asp Asn Ile Asn Asn Ile Asn Gly Asn Asn
1               5                   10                  15

Asn Asn His Asp Asn Asn His Asp Asn Asn Asn Asn Ile Asn Gly
            20                  25                  30

Asn Asn

<210> SEQ ID NO 25
<211> LENGTH: 34
<212> TYPE: PRT
<213> ORGANISM: Artificial Sequence
<220> FEATURE:
<223> OTHER INFORMATION: Synthetic

<400> SEQUENCE: 25

Asn Asn His Asp Asn Asn His Asp Asn Ile Asn Ile Asn Gly Asn Gly
1               5                   10                  15

Asn Asn His Ala Asn Ile Asn Gly His Asp His Asp Asn Ile Asn Asn
            20                  25                  30

Asn Asn

<210> SEQ ID NO 26
<211> LENGTH: 34
<212> TYPE: PRT
<213> ORGANISM: Artificial Sequence
<220> FEATURE:
<223> OTHER INFORMATION: Synthetic

<400> SEQUENCE: 26

Asn Asn His Asp Asn Ile Asn Gly Asn Asn His Asp Asn Ile His Asp
1               5                   10                  15

His Asp Asn Asn His Asp Asn Gly Asn Gly His Asp Asn Gly Asn Asn
            20                  25                  30

His Asp

<210> SEQ ID NO 27
<211> LENGTH: 40
<212> TYPE: PRT
<213> ORGANISM: Artificial Sequence
<220> FEATURE:
<223> OTHER INFORMATION: Synthetic
```

```
<400> SEQUENCE: 27

Asn Asn Asn Asn His Asp His Asp Asn His Asp His Asp Asn Ile
1               5                   10                  15

His Asp His Asp Asn Asn Asn Asn His Asp His Asp Asn Asn Asn Gly
                20                  25                  30

Asn Asn Asn Ile His Asp Asn Asn
        35              40

<210> SEQ ID NO 28
<211> LENGTH: 40
<212> TYPE: PRT
<213> ORGANISM: Artificial Sequence
<220> FEATURE:
<223> OTHER INFORMATION: Synthetic

<400> SEQUENCE: 28

His Asp Asn Asn His Asp His Asp Asn Asn His Asp Asn Asn His Asp
1               5                   10                  15

His Asp His Asp Asn Asn His Asp His Asp Asn Asn Asn Asn His Asp
                20                  25                  30

His Asp His Asp Asn Ile Asn Asn
        35              40

<210> SEQ ID NO 29
<211> LENGTH: 40
<212> TYPE: PRT
<213> ORGANISM: Artificial Sequence
<220> FEATURE:
<223> OTHER INFORMATION: Synthetic

<400> SEQUENCE: 29

Asn Asn Asn Asn Asn Gly His Asp Asn Ile Asn Asn His Asp Asn Ile
1               5                   10                  15

Asn Asn Asn Asn Asn Ile Asn Ile Asn Asn His Asp His Asp His Asp
                20                  25                  30

Asn Gly Asn Gly His Asp Asn Gly
        35              40

<210> SEQ ID NO 30
<211> LENGTH: 30
<212> TYPE: PRT
<213> ORGANISM: Artificial Sequence
<220> FEATURE:
<223> OTHER INFORMATION: Synthetic

<400> SEQUENCE: 30

Asn Asn Asn Asn His Asp His Asp Asn Ile Asn Gly Asn Asn Asn Ile
1               5                   10                  15

Asn Asn His Asp His Asp Asn Asn His Asp His Asp Asn Asn
                20                  25                  30
```

MATERIALS AND METHODS FOR THE TREATMENT OF LATENT VIRAL INFECTION

This invention was made with government support under R01 AI097376 awarded by National Institutes of Health. The government has certain rights in the invention.

CROSS-REFERENCE TO RELATED APPLICATIONS

This application is the U.S. national stage application of International Patent Application No. PCT/US2015/024094, filed Apr. 2, 2015, which claims the benefit of U.S. Provisional Application Ser. No. 61/973,995, filed Apr. 2, 2014, the disclosures of which are hereby incorporated by reference in their entirety, including all figures, tables and amino acid or nucleic acid sequences.

The Sequence Listing for this application is labeled "Seq-List.txt" which was created on Apr. 2, 2015 and is 13 KB. The entire contents of the sequence listing is incorporated herein by reference in its entirety.

BACKGROUND OF THE INVENTION

Herpes simplex virus 1 (HSV-1) is a human pathogen that efficiently establishes lifelong infections that can manifest as a variety of disease states that vary depending on the host and the site of infection. These diseases include orolabial herpes, presenting with the recurrence of painful and psychologically distressing cold sores around the lips, and herpes keratitis, in which recurrence in the eye results in inevitable loss of vision, making HSV-1 the leading cause of infectious blindness in the developed world. Between 50-90% of adults in the U.S. are estimated to be infected with HSV-1, with incidence approaching 100% for the subpopulation over the age of 60. While the majority of hosts are asymptomatic, viral shedding occurs spontaneously, resulting in propagation of infection. Similar to HSV-1, HSV-2 also establishes a lifelong infection, with a greater prevalence for recurrence at the genital mucosa.

Following local replication at the site of primary infection with either virus, the virus enters into the nervous system via sensory nerve termini. Once in the nuclei of sensory ganglia neurons, the ≈153 kb HSV-1 double stranded linear DNA genome enters into a closed circular episomal form. The episome rapidly becomes associated with cellular histones that largely bear epigenetic modifications associated with transcriptional repression, resulting in the transcriptional inactivity of lytic genes that is the hallmark of latency. However, in defined regions of the genome, histones are associated with permissive histone modifications, which allow for accessibility to the DNA, and low levels of transcription. This transcription permits the accumulation of the only transcript abundantly expressed during latency, the latency-associated transcript (LAT), as well as a number of HSV-1 encoded microRNAs (miRNAs). Together, these transcripts are thought to play a role in the regulation of viral latency and reactivation. Spontaneously, and/or in response to a multitude of stressors, the HSV-1 episome undergoes reactivation, resulting in a lytic cascade of gene expression, replication of the viral genome, and subsequent egress of infectious virions.

Antivirals exist with broad activity against herpesvirus DNA replication, and these present the U.S. with an economic burden of over $500,000,000 annually. Importantly, these antivirals only limit the duration of reactivation events when used reactively, or limit the frequency of reactivation events when used proactively, while neither impacting latent infection nor allowing for a reduction/cure of the viral burden. HSV can develop resistance to commonly used antivirals such as acyclovir, and HSV is also not amenable to traditional vaccination schemes. Alternative chemotherapeutic treatments for latent infection are impeded by the absence of protein targets produced by the quiescent virus.

This disclosure seeks to alleviate these issues by providing distinct approaches to treat and/or cure latent viral infections, such as HSV-1 and HSV-2 infections, by significantly reducing or eliminating the latent viral load and thus reducing or eliminating recurrent disease. While these approaches are described using HSV-1 as a model pathogen in this application (owing to its simpler laboratory manipulation), nearly identical methods are adaptable to other viruses, such as HSV-2, other neurotropic herpes viruses (including Varicella zoster virus (VZV), the causative agent of shingles and post-herpetic neuralgia) and other viruses.

BRIEF SUMMARY OF THE INVENTION

A first aspect of the invention relates to materials and methods of using synthetic Transcription activator-like (TAL) binding domains that include "effector" domains. In the case of TAL effector nucleases (TALENs), the effector domain is the DNA cleavage domain from an endonuclease (such as FokI), which requires dimerization for activity. To utilize TALEN-mediated DNA cleavage, a pair of TALEN are designed to bind at sequences flanking a chosen target site such that the endonuclease domains (FokI domains for example) of each TALEN meet, dimerize, and catalyze cleavage at the desired target site. Following cleavage, the resulting double-strand break (DSB) can be repaired via non-homologous end joining (NHEJ). NHEJ is commonly imperfect, resulting in a mutation at the site of cleavage. Alternatively, if NHEJ repairs the DSB perfectly, the product will be reiteratively cleaved by the TALENs until some form of mutation is generated. When such mutations occur in important coding regions of the target genome, the result is a loss-of-function mutation of the relevant gene. In some circumstances, cleavage of episomes can result in destabilization and loss of the DNA.

A second aspect of the invention provides materials and methods for the treatment of latent viral infections by fusing TAL to an effector domain comprising a transcriptional activation domain (TALTADs), such as the strongly transactivating domain found in the HSV-1 VP16 protein. When such domains are fused to TAL DNA-binding components, effectors are targeted to the 5' promoter regions of particular genes. The resulting TAL-VP16 fusion protein acts to drive transcription from that gene. Other viral transactivating domains can also be used in this aspect of the invention for the treatment of different viral diseases.

A third aspect of the invention relates to materials and methods for the cleavage of viral nucleic acids, such as HSV-1 episomes in vivo and in vitro) that utilize RNA guided dsDNA endonuclease (RGN), such as a Type II CRISPR/Cas system. As an example, Cas9, a bacterial RNA guided dsDNA endonuclease (RGN), can be directed to bind and cleave specific DNA sequences using a short guide RNA (gRNA) expressed in trans. In this aspect of the invention, the RGN, such as a Type II CRISPR/Cas, is packaged in an AAV vector. RGN, such as a II CRISPR/Cas9, can be expressed by using small promoters to drive expression.

BRIEF DESCRIPTION OF THE DRAWINGS

The patent or application file contains at least one drawing executed in color. Copies of this patent or patent application publication, with color drawing(s), will be provided by the Office upon request and payment of the necessary fee.

FIGS. 2A-2C. Cleavage of HSV-1 DNA. A) Schematic of the indicator constructs used in this analysis, with the HSV-1 TALEN target cloned between the Rev and a GFP open reading frames. B) Detection of GFP expression in cells co-transfected with an indicator construct (control of HSV-1 based) and a TALEN pair (control or HSV-1 specific). Each TALEN is able to block expression of GFP from the cognate target. C) Western analysis of cells co-transfected with the Rev-GFP indicator and TALENs. The miR-H1 HSV-1 target and both ICP0 targets are specifically cleaved by their cognate TALENs, resulting in loss of protein expression.

FIGS. 7A-7D. NMCas9 is a highly efficient nuclease in human cells. FIGS. 7A and 7B describe the guide RNA chimera design adopted for use in this work. Red overlined text represents the specific targeting sequence motif. Dark blue text represents the tracrRNA portion fused to the crRNA with the teal GAAA tetraloop. FIG. 7C—Microscopy for eGFP positive cells shows cleavage specific reduction or elimination of fluorescence. F. 7D shows a Western blot with anti-FLAG demonstrating NMCas9 expression in human 293T cells (upper panel), and, in the lower panel, gRNA specific ablation of Rev:GFP fusion protein expression, demonstrating NMCas9 function.

DETAILED DISCLOSURE OF THE INVENTION

Figure 1:
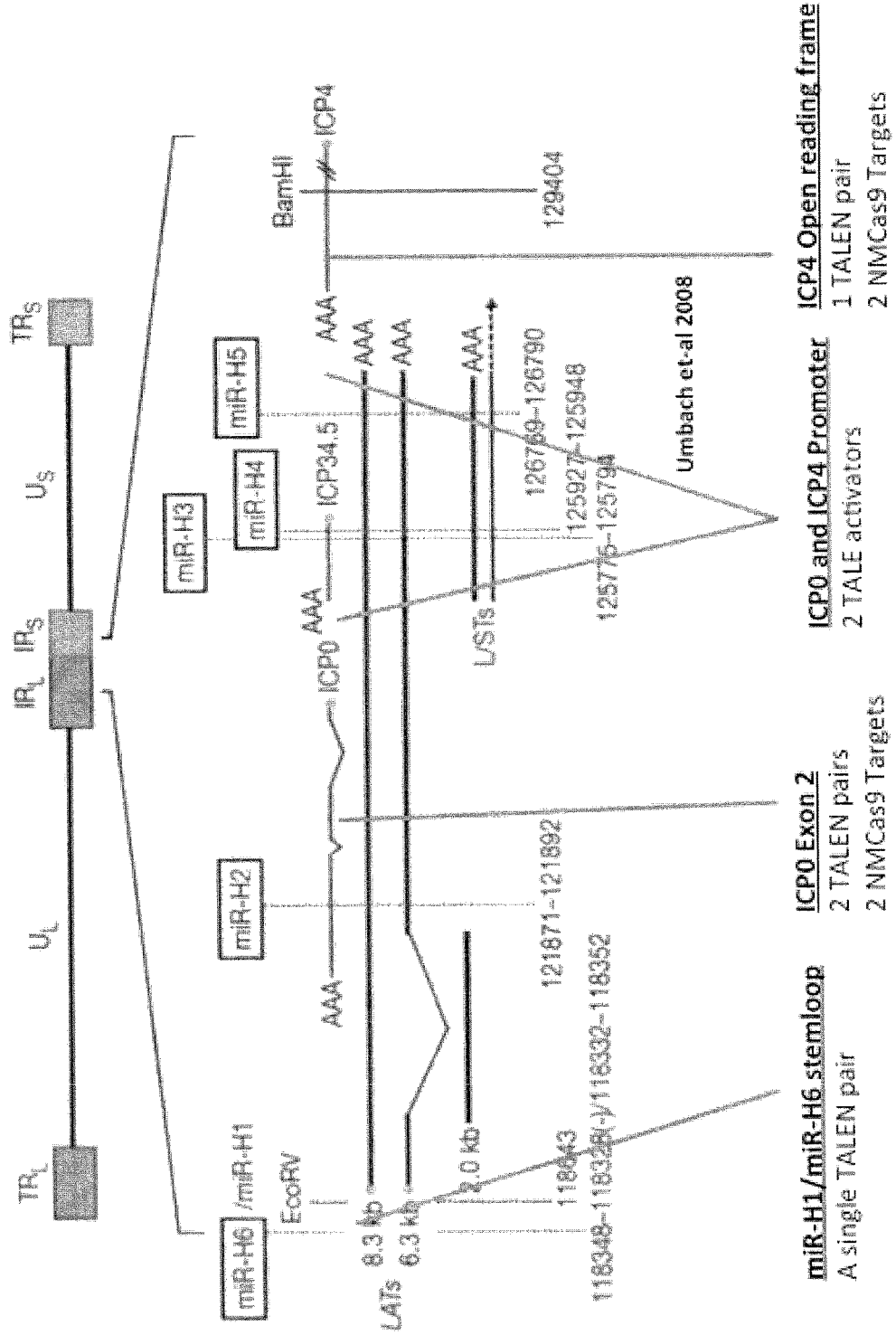
FIG. 1. Schematic of the HSV-1 genome and targeted regions. The HSV-1 DNA genome is ~153 kb in length and consists of terminal repeats (TRs), internal repeats (IRs) and unique long ($U_L$) and unique short ($U_S$) segments (upper panel). The only region that is transcriptionally active, and hence accessible, in latently infected cells is adjacent to the viral LAT gene. LAT is in turn antisense to the ICP0 immediate early gene and adjacent to ICP0. The TALENs and NMCas9 RGN constructs designed so far are able to cleave the HSV-1 genome in the exonic region of ICP0 and ICP4, and within the miR-H6/miR-H1 microRNA stem-loop. TALE-VP16 fusions are able to bind and activate either the ICP0 or ICP4 promoter.

The terms "nucleic acid," "polynucleotide," and "oligonucleotide" (and grammatical variants thereof) are used interchangeably and refer to a deoxyribonucleotide or ribonucleotide polymer, in linear or circular conformation, and in either single- or double-stranded form. For the purposes of the present disclosure, these polymers are not limited in length. Analogs and/or nucleotides that are modified in the base, sugar and/or phosphate moieties (e.g., phosphorothioate backbones) of natural nucleotides may be included in the polymers. Analogs will have the same base-pairing specificity as occurs in nature (an analog of G will base-pair with C).

The terms "polypeptide," "peptide" and "protein" (and grammatical variants thereof) are used interchangeably to refer to a polymer of amino acid residues. The term also applies to amino acid polymers in which one or more amino acids are chemical analogues or modified derivatives of corresponding naturally-occurring amino acids.

"Binding" and grammatical variants thereof (e.g., bind, binds, bound, etc.) refers to a sequence-specific, non-covalent interaction between macromolecules (e.g., between a protein (e.g., a TAL) and a nucleic acid or an antibody with its cognate antigen/epitope).

A "binding protein" (and grammatical variants thereof) is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A polypeptide having an activity on nucleic acids is defined as an "effector domain(s)" herein. Effector domains can be modified by being combined with a TAL as described herein in order to cause an effect at a target site within the genome of an organism that is bound by the TAL. Examples of such polypeptides include, and are not limited to, transcription activator (also referred to as transcription activator domain(s); TAD(S)) and repressor proteins, nucleases, topoisomerases, ligases, integrases, recombinases, resolvases, methylases, acetylases, demethylases, deacetylases, and any other polypeptide capable of modifying DNA or RNA. In certain preferred embodiments, the polypeptides combined with a TAL are nucleases such as MmeI, Colicin-E7 (CEA7_ECOLX), EndA, Endo I (END1_ECOLI), Human Endo G (NUCG HUMAN), Bovine Endo G (NUCG_BOVIN), R.HinPI I, I-BasI, I-BmoI, I-HmuI, I-Tev-I, I-TevII, I-TevIII, I-TwoI, R.MspI, R.MvaI, NucA, NucM, Vvn, Vvn_CLS, Staphylococcal nuclease (NUC_STAAU), Staphylococcal nuclease (NUC_STAHY), Micrococcal nuclease (NUC_SHIFL), Endonuclease yncB, Endodeoxyribonuclease I (ENRN_BPT7), Metnase, Nb.BsrDI, BsrDI A, Nt.BspD6I (R.BspD6I large subunit), ss.BspD6I (R.BspD6I small subunit), R.PleI, MlyI, AlwI, Mva1269I, BsrI, BsmI, Nb.BtsCI, Nt.BtsCI, RlBtsI, R2.BtsI, BbvCI subunit 1, BbvCI subunit 2, BpuIOI alpha subunit, BpuIOI beta subunit, BmrI, BfiI, I-CreI, hExoI (EX01JHUMAN), Yeast ExoI (EX01_YEAST), *E. coli* ExoI, Human TREX2, Mouse TREX1, Human TREX1, Bovine TREX1, Rat TREX1, Human DNA2, Yeast DNA2 (DNA2_YEAST), VP16, RBBP8 and Type IIS nucleases like Fok-I. In certain preferred embodiments, the nuclease is Fok-I.

Trans-activating domains (TAD(S)) include, and are not limited to, polypeptides containing a nine-amino-acid trans-activation domain (9aaTAD) that defines a novel domain common to a large superfamily of eukaryotic transcription factors. Non-limiting examples of such eukaryotic transcription factors include p53 (also known as cellular tumor antigen p53, phosphoprotein p53, or tumor suppressor p53 which is encoded by the TP53 gene) or a fragment of p53 comprising amino acids 1-42, NFAT (Nuclear factor of activated T-cells), NF-κB (nuclear factor kappa-light-chain-enhancer of activated B cells), E1A (adenovirus transcriptional activator) and VP16 (α-TIF (also known as Trans Inducing Factor).

Targeting Effector Molecules (TALENS and TALTADS). Transcription activator-like (TAL) binding domains are natively expressed by bacteria of the *Xanthomonas* genus and utilize a protein-DNA interaction mediated by a unique DNA-binding motif that is an array of highly conserved 34-amino acid repeats, where each of the repeats mediates binding to a single nucleotide base pair. The targeted base pair is determined by the identity of the $12^{th}$ and $13^{th}$ amino acid in each repeat. Owing to the relationship between the amino acid sequence of the TAL binding domain and the DNA target sequence, synthetic TAL effectors with permutated repeats have been developed with exquisite specificity towards target genes. TAL binding domains can be "engineered" to bind to a predetermined nucleotide sequence, Non-limiting examples of methods for engineering DNA-binding proteins are design and selection. A designed DNA binding protein is a protein not occurring in nature whose design/composition results principally from rational criteria. Methods of engineering TAL and other nucleic acid binding domains, such as zinc finger proteins, to bind a predetermined nucleic acid sequence are known in the art (see, for example, U.S. Pat. Nos. 6,140,081; 6,453,242; and 6,534, 261; see also WO 98/53058; WO 98/53059; WO 98/53060; WO 02/016536 and WO 03/016496 and U.S. Patent Application Publication No. 20110301073, each of which is hereby incorporated by reference in its entirety for such purposes).

TAL binding domains (synthetic or engineered) effectors can include various "effector domains" (as discussed above). In the case where a TAL is associated with an nuclease, the TAL effector is referred to as a TALEN. Thus, the effector domain can be any of the nucleases (e.g., an endonuclease) discussed above. In certain embodiments, the nuclease/endonuclease attached to the TAL can be a nuclease/endonuclease that requires dimerization for activity (e.g., Fok-I) or can be an nuclease/endonuclease that does not require dimerization for activity. To utilize TALEN-mediated DNA cleavage with an endonuclease that requires dimerization for activity, a pair of TALENs are designed to bind at sequences flanking a chosen target site such that the endonuclease domains of each TALEN meet, dimerize, and catalyze cleavage at the desired target site. An exemplary endonuclease in this aspect of the invention is Fok-I. In other embodiments, engineered nucleases can be used to form a TALEN pair. In these embodiments, the nucleases have been modified to form obligate heterodimers with nuclease. Examples of such nucleases can be found in U.S. Patent Publication Nos. 2005/0064474, 2007/0218528, 2008/0131962 and 2011/0201055, each of which is hereby incorporated herein by reference in its entirety. Exemplary amino acid sequences that provide binding specificity to target genes within TAL are provided below (in single letter amino acid code). All the coordinates are chosen out of the GenBank genomic sequence of the HSV-1 strain 17syn+ and this sequence can be accessed on GenBank using the accession number NC_001806 (which is hereby incorporated by reference in its entirety). TAL binding domains can be assembled using the REAL TALEN Assembly Kit or the Voytas Golden Gate Assembly Kit. The target coordinates for each TAL fusion protein are shown in the HSV-1 genome. Since ICP0 and ICP4 each occur twice in the viral genome, the genes are coded on one DNA strand in one direction (+, sense) and in the other second gene is coded on the other DNA strand in an opposing direction (−, antisense).

```
RA-TALEN_ICP0_S1:

Assembled Using:       REAL Assembly Kit
Functional Domain:     FokI (wt)
RVD Sequence:          NN-HD-NN-HD-NI-NI-NG-NG-NN-HD-NI-NG-HD-HD-
                       NI-NN-NN (SEQ ID NO: 19)
DNA Target Sequence:   5'-gcgcaattgcatccagg-3' (SEQ ID NO: 2)
DNA Target Coordinates: 3459-3475 (-), 122896-122912 (+)
DNA Target Gene:       ICP0 exon

RA-TALEN_ICP0_S2:

Assembled Using:       REAL Assembly Kit
Functional Domain:     FokI (wt)
RVD Sequence:          NN-HD-NI-NG-NN-HD-NI-HD-HD-NN-HD-NG-NG-HD-
                       NG-NN-HD (SEQ ID NO: 20)
DNA Target Sequence:   5'-gcatgcaccgcttctgc-3' (SEQ ID NO: 3)
DNA Target Coordinates: 3426-3442 (+), 122929-122945 (-)
DNA Target Gene:       ICP0 exon

GG-TALEN_ICP4_S1:

Assembled Using:       Golden Gate Assembly Kit
Functional Domain:     FokI (wt)
RVD Sequence:          NN-NN-HD-HD-NH-HD-HD-NI-HD-HD-NH-NH-HD-HD-
                       NH-NG-NH-NI-HD-NN (SEQ ID NO: 21)
DNA Target Sequence:   5'-ggccgccaccggccgtgacg-3' (SEQ ID NO: 4)
DNA Target Coordinates: 130605-130624 (+), 147609-147628 (-)
DNA Target Gene:       ICP4 coding region

GG-TALEN_ICP4_S2:

Assembled Using:       Golden Gate Assembly Kit
Functional Domain:     FokI (wt)
RVD Sequence:          HD-NN-HD-HD-NH-HD-NH-HD-HD-HD-NH-HD-HD-NH-
                       NH-HD-HD-HD-NI-NN (SEQ ID NO: 22)
DNA Target Sequence:   5'-cgccgcgcccgccggcccag-3' (SEQ ID NO:5)
DNA Target Coordinates: 130640-130659 (-), 147574-147593 (+)
DNA Target Gene:       ICP4 coding region

RA-TALE_ICP0:

Assembled Using:       REAL Assembly Kit
Functional Domain:     VP16
RVD Sequence:          NN-NN-NN-NI-HD-NN-HD-NN-HD-NN-NN-HD-HD-NI-
                       NG (SEQ ID NO: 23)
DNA Target Sequence:   5'-gggacgcgcggccat-3' (SEQ ID NO: 6)
DNA Target Coordinates: 2023-2037 (+), 124334-124348 (-)
DNA Target Gene:       ICP0 promoter

RA-TALE_ICP4:

Assembled Using:       REAL Assembly Kit
Functional Domain:     VP16
RVD Sequence:          NN-NN-HD-NI-NN-NI-NG-NN-NN-HD-NN-HD-NN-NN-
                       NI-NG-NN (SEQ ID NO: 24)
DNA Target Sequence:   5'-ggcagatggcgcggatg-3' (SEQ ID NO: 7)
DNA Target Coordinates: 131620-131636 (-), 146597-146613 (+)
DNA Target Gene:       ICP4 promoter.
```

A second possible effector domain for synthetic TAL effectors is a transcriptional activation domain, such as the strongly transactivating domain VP16 protein. These synthetic TAL effectors are referred to as TALTAD(s). TALTAD(s) are targeted to the 5' promoter regions of a particular target gene and the resulting fusion protein (e.g., TALE-VP16) acts to drive transcription from that gene. Such TAL effectors can be used in combination with anti-viral chemotherapeutic agents for the treatment of the viral infection. Non-limiting examples of anti-viral agents include trifluordine, docosanol, acyclovir, famciclovir, ganciclovir, penciclovir and valacyclovir.

In certain embodiments of methods for targeted alteration of a sequence in a region of interest in viral nucleic acids, either episomal or incorporated into the genome, of the subject to be treated. Any of the methods described herein can be used for partial or complete inactivation of one or more viral target sequences in a cell. In addition these methods may be directed to mutate the target protein such that it may be expressed but is non-functional and could actively interfere with the activity of other non-mutated viral proteins present in that cell (dominant-negative mutation).

The term "sequence" (and grammatical variants thereof) refers to a nucleotide sequence of any length, which can be DNA or RNA. The nucleotide sequence can be linear, circular (e.g., episomal) or branched and can be either single-stranded or double stranded. An "episome" is a replicating nucleic acid, nucleoprotein complex or other structure comprising a nucleic acid that is not part of the chromosomal karyotype of a cell. Examples of episomes include plasmids and certain viral genomes.

A "target site" or "target sequence" (and grammatical variants thereof) is a nucleic acid sequence that defines a portion of a nucleic acid to which a binding molecule will bind, provided sufficient conditions for binding exist. In various embodiments, the target sequences can be viral genes (also referred to as "a target gene" or "target genes") that are associated with transcriptional activation of latent viruses within a cell. Non-limiting examples of such genes include ICP27, ICP0 and ICP4 for HSV-1 and HSV-2. Other target sequences include, and are not limited to, genes associated with replication of the viral genome (e.g., UL5, UL7, etc.), polymerases (e.g., UL30) and genes associated with processing and packaging of viral DNA (e.g., UL25) or producing viral RNAs during latency. Similar target sequences can be identified in other viruses causing latent infections from genomes found in databases such as EMBL or GenBank.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. An exogenous molecule can be, among other things, a viral protein produced by a virus in either its latent state or while causing active infection.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

A "fusion molecule" or "fusion protein" (and grammatical variants thereof) is a molecule in which two or more subunit molecules are linked, preferably covalently. The subunit molecules can be the same chemical type of molecule (e.g., two or more proteins) or can be different chemical types of molecules (e.g., a nucleic acid and a protein). Examples of the first type of fusion molecule include, but are not limited to, TALEN or TALTAD fusion proteins. Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Methods for polynucleotide and polypeptide delivery to cells are presented elsewhere in this disclosure.

"Modulation" of gene expression refers to a change in the activity of a gene. Modulation of expression can include, but is not limited to, gene activation and gene repression. "Gene inactivation" refers to any reduction in gene expression as compared to a cell that does not include TALEN, TALTAD or other TAL binding domain fused to an effector domain as described herein. "Gene activation" refers to any increase in gene expression as compared to a cell that does not include TALEN, TALTAD or other TAL binding domain fused to an effector domain as described herein. Thus, gene activation/inactivation may be partial or complete. Gene activation or inactivation can also be modulated by a RGN as described herein.

A "region of interest" is any region of cellular chromatin, such as, for example, a gene or a non-coding sequence within or adjacent to a gene, in which it is desirable to bind a TAL binding domain fused to an effector domain as described herein (or a RGN). Binding can be for the purposes of targeted DNA cleavage and/or targeted delivery of an effector domain as described herein. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region (e.g., a promoter upstream of a coding region). A region of interest can be as small as a single nucleotide pair or up to 2,000 nucleotide pairs in length, or any integral value of nucleotide pairs.

The terms "operatively linked" or "operably linked" can be used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. With respect to fusion polypeptides, the term "operatively linked" can refer to the fact that each of the components performs the same function in linkage to the other component as it would if it were not so linked. For example, with respect to a fusion protein comprising a TAL binding domain fused to an effector domain polypeptide the individual elements of the fusion protein are in operative linkage if, in the fusion protein, the TAL binding domain is able to bind its target site and/or its binding site, while the effector domain able to mediate its effect on gene expression (e.g., up-regulation of gene expression by a transcription activation factor, cleavage of a nucleic acid sequence by a nuclease or methylation of a nucleic acid sequence or nucleotide).

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one or more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis or other methods known in the art.

The CRISPR/Cas System

The Type II CRISPR (exemplified by Cas9) is a well characterized system and carries out targeted DNA double-strand break in four sequential steps. First, two non-coding RNA, the pre-crRNA array and tracrRNA, are transcribed from the CRISPR locus. Second, tracrRNA hybridizes to the repeat regions of the pre-crRNA and mediates the processing of pre-crRNA into mature crRNAs containing individual spacer sequences. Third, the mature crRNA:tracrRNA complex directs Cas9 to the target DNA via Watson-Crick base-pairing between the spacer on the crRNA and the protospacer on the target DNA next to the protospacer adjacent motif (PAM), an additional requirement for target recognition. Finally, Cas9 mediates cleavage of target DNA to create a double-stranded break within the protospacer.

In type II CRISPR/Cas systems, crRNAs are produced using a different mechanism where a trans-activating RNA (tracrRNA) complementary to repeat sequences in the pre-crRNA, triggers processing by a double strand-specific RNase III in the presence of the Cas9 protein. Cas9 is then able to cleave a target DNA that is complementary to the mature crRNA however cleavage by Cas 9 is dependent both upon base-pairing between the crRNA and the target DNA, and on the presence of a short motif in the crRNA referred to as the PAM sequence (protospacer adjacent motif) (see Qi et al. (2013) *Cell* 152:1173). In addition, the tracrRNA must also be present as it base pairs with the crRNA at its 3' end, and this association triggers Cas9 activity.

Type II CRISPR/Cas systems can be delivered to target sites using guide RNA. These guide RNA are referred to as "single-guide RNA" (gRNA) that contain the hairpin normally formed by the annealing of the crRNA and the tracrRNA. In certain embodiments, Cas protein may be a "functional derivative" of a naturally occurring Cas protein. A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity in common with a corresponding native sequence polypeptide. A biological activity contemplated herein is the ability of the functional derivative to hydrolyze a DNA substrate into fragments. The term "derivative" encompasses both amino acid sequence variants of polypeptide, covalent modifications, and fusions thereof. Examples of guide sequences for HSV-1 are provided below:

```
ICP4-G1
                                           (SEQ ID NO: 8)
GCGGTGGCCGGCCGCGACGCCACG;

Target (gRNA + PAM)
                                           (SEQ ID NO: 9)
GCGGTGGCCGGCCGCGACGCCACGGGCCGCTT;

ICP4-G2
                                          (SEQ ID NO: 10)
GCCGCGGCCGGAGGGACCCGCGGG;

Target (gRNA + PAM)
                                          (SEQ ID NO: 11)
CCCGCGGCCGGAGGGACCCGCGGGCCCCGCTT;

ICP4-G3
                                          (SEQ ID NO: 12)
GGGGGGCCCTGCCGCCGGCGCCGC;

Target (gRNA + PAM)
                                          (SEQ ID NO: 13)
CGGGGGCCCTGCCGCCGGCGCCGCCCGGGATT;

ICP0-G1
                                          (SEQ ID NO: 14)
GGGGTCAGGTACCGCGGGGCGAAC;

Target (gRNA + PAM)
                                          (SEQ ID NO: 15)
AGGGTCAGGTACCGCGGGGCGAACCGCTGATT;

ICP0-G2
                                          (SEQ ID NO: 16)
GGCGTCACGCCCACTATCAGGTAC;

Target (gRNA + PAM)
                                          (SEQ ID NO: 17)
GGCGTCACGCCCACTATCAGGTACACCAGCTT.
```

The term "Cas polypeptide" encompasses a full-length Cas polypeptide, an enzymatically active fragment of a Cas polypeptide, and enzymatically active derivatives of a Cas polypeptide or fragment thereof. Suitable derivatives of a Cas polypeptide or a fragment thereof include but are not limited to mutants, fusions, covalent modifications of Cas protein or a fragment thereof.

Cas proteins and Cas polypeptides may be obtainable from a cell or synthesized chemically or by a combination of these two procedures. The cell may be a cell that naturally produces Cas protein, or a cell that naturally produces Cas protein and is genetically engineered to produce the endogenous Cas protein at a higher expression level or to produce a Cas protein from an exogenously introduced nucleic acid, which nucleic acid encodes a Cas that is same or different from the endogenous Cas. In some case, the cell does not naturally produce Cas protein and is genetically engineered to produce a Cas protein.

The CRISPR/Cas system can also be used to inhibit gene expression. For example, a catalytically inactive Cas9 (i.e., a Cas9 lacking endonuclease activity) generates a DNA recognition complex that can specifically interfere with transcriptional elongation, RNA polymerase binding, or transcription factor binding when co-expressed with a guide RNA. This system, called CRISPR interference (CRISPRi), can efficiently repress expression of targeted genes. Additionally, Cas proteins have been developed which comprise mutations in their cleavage domains to render them incapable of inducing a DSB, and instead introduce a nick into the target DNA ("Cas9 nicking enzyme").

A polynucleotide can be introduced into a cell as part of a vector molecule having additional sequences such as, for example, replication origins, promoters and genes encoding antibiotic resistance or other marker genes. Marker genes include, but are not limited to, sequences encoding proteins that mediate antibiotic resistance (e.g., ampicillin resistance, neomycin resistance, G418 resistance, puromycin resistance), sequences encoding colored or fluorescent or luminescent proteins (e.g., green fluorescent protein, enhanced green fluorescent protein, red fluorescent protein, luciferase), and proteins which mediate enhanced cell growth and/or gene amplification (e.g., dihydrofolate reductase). Epitope tags include, for example, one or more copies of FLAG, His, myc, Tap, HA or any detectable amino acid sequence.

The fusion proteins and CRISPR/Cas systems disclosed herein can be delivered in vivo or ex vivo by any suitable means. For example, any vector system may be used including, but not limited to, plasmid vectors, retroviral vectors, lentiviral vectors, adenovirus vectors, poxvirus vectors; herpesvirus vectors and adeno-associated virus vectors, etc. (see, for example, U.S. Pat. Nos. 6,534,261; 6,607,882; 6,824,978; 6,933,113; 6,979,539; 7,013,219; and 7,163,824, each of which is hereby incorporated by reference herein in its entirety). Furthermore, it will be apparent that any of these vectors may comprise one or more of the sequences needed for treatment. Thus, when one or more fusion protein or CRISPR/Cas system are introduced into the cell, the fusion proteins and/or CRISPR/Cas system may be carried on the same vector or on different vectors. When multiple vectors are used, each vector may comprise a sequence encoding one or fusion protein or CRISPR/Cas system.

Conventional viral and non-viral based gene transfer methods can be used to introduce nucleic acids into cells (e.g., mammalian cells) and target tissues. Non-viral vector delivery systems include DNA plasmids, naked nucleic acid, and nucleic acid complexed with a delivery vehicle such as a liposome or poloxamer. Viral vector delivery systems include DNA and RNA viruses, which have either episomal or integrated genomes after delivery to the cell. Methods of non-viral delivery of nucleic acids include electroporation, lipofection, microinjection, biolistics, virosomes, liposomes, immunoliposomes, polycation or lipid:nucleic acid conjugates, naked DNA, artificial virions, and agent-enhanced uptake of DNA.

In situations in which transient expression is preferred, adenoviral based systems can be used. Adenoviral based vectors are capable of very high transduction efficiency in many cell types and do not require cell division. With such vectors, high titer and high levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures. Construction of recombinant AAV vectors are generally known to those skilled in the art.

Recombinant adeno-associated virus vectors (rAAV) are a promising alternative gene delivery systems based on the defective and nonpathogenic parvovirus adeno-associated type 2 virus. All vectors are derived from a plasmid that retains only the AAV 145 bp inverted terminal repeats flanking the transgene expression cassette. Efficient gene transfer and stable transgene delivery due to integration into the genomes of the transduced cell are key features for this vector system. Other AAV serotypes, including AAV1, AAV3, AAV4, AAV5, AAV6, AAV8, AAV9 and AAVrh10, and all variants thereof, can also be used in accordance with the present invention.

Gene therapy vectors can be delivered in vivo by administration to an individual subject, typically by systemic administration (e.g., intravenous, intraperitoneal, intramuscular, subdermal, or intracranial infusion) or topical application.

Pharmaceutically acceptable carriers are determined in part by the particular composition being administered, as well as by the particular method used to administer the composition. Accordingly, there is a wide variety of suitable formulations of pharmaceutical compositions available, as described below (see, e.g., Remington's Pharmaceutical Sciences, 17th ed., 1989).

Viruses causing latent infections: The majority of viruses that cause latent infections are of the family Herpesviridae. These include, and are not limited to, herpes simplex virus (HSV)-1, HSV-2, varicella zoster virus (VZV), Epstein-Barr virus (EBV), CMV, human herpesvirus (HHV)-6, HHV-7 and Kaposi's sarcoma-associated herpesvirus (KSHV/HHV)-8. Other examples of viruses that cause latent infections include JC and BK virus (from the family Polyomaviridae), adenovirus (Adenoviridae) and parvovirus and adeno-associated virus (AAV; Parvoviridae). Thus, the subject disclosure seeks to provide methods of treating such viral infections comprising the administration of fusion proteins or CRISPR/Cas systems disclosed herein.

The terms "treat", "treating", "treatment" and various grammatical variants thereof refer to reducing the frequency of reactivation events for treated subjects/patients. In some embodiments, it may be possible to eliminate the recurrence of reactivation episodes entirely.

Thus, a further aspect of the invention relates to the treatment of latent viral infections using TALEN(s) or TALTAD(s). Thus, in this aspect of the invention, TALEN(s) are administered to a subject having a latent viral infection in an amount effective to either bind and mutagenize/inactivate (or cause the degradation) of latent viral episomes or integrated viral genomes within a cell) or TALTAD(s) are administered to a subject having a latent viral infection in an amount effective drive the viral episome or integrated viral genome from a dormant state into one of productive replication. Where TALTAD(s) are administered to drive expression of the viral episome or integrated viral genome into productive replication, the subject is also treated with an antiviral drug, such as acyclovir, that blocks viral replication at the stage of viral DNA synthesis. Latent viral infections suitable for treatment in accordance with this disclosure include, but are not limited to, herpes simplex virus (HSV)-1, HSV-2, varicella zoster virus (VZV), Epstein-Barr virus (EBV), CMV, human herpesvirus (HHV)-6, HHV-7, Kaposi's sarcoma-associated herpesvirus (KSHV/HHV)-8, JC and BK virus (from the family Polyomaviridae), adenovirus (Adenoviridae), parvovirus and adeno-associated virus (AAV; Parvoviridae).

Yet another aspect of the invention provides methods for treatment of latent viral infections comprising the administration of a Type II Clustered Regularly Interspaced Short Palindromic Repeats (CRISPR)/Cas system to cleave latent viral episomes in vivo or in vitro. There are two distinct elements to the (CRISPR)/Cas system. These are: (1) a guide RNA (gRNA) and (2) an endonuclease (e.g., a Cas nuclease such as Cas9). The gRNA/Cas9 complex base-pairs with a target sequence in episomal or genomic DNA. Thus, Cas9 is directed to bind and cleave specific DNA sequences using a short gRNA. In certain embodiments, the guide sequences can bind to any desired nucleic acid sequence found in the genome of a virus causing latent infection. For HSV viruses, preferred genes include AAV is a small ssDNA virus that has been extensively employed as a gene therapy vector, owing to advantages including its broad cellular tropism, prolonged transduction in dividing and non-dividing cells, and lack of pathogenicity or affinity for insertional mutagenesis. We are able to generate AAV viral vector stocks with titers of $\approx 10^{13}$ infectious units per mL, and we have established a facile and non-invasive AAV delivery protocol enacted via topical delivery at the peripheral epithelium. Through this method, transduction can be achieved in ≥98% of all sensory neurons in the dorsal root ganglia of mice, or >80% of trigeminal ganglia neurons of rabbits, demonstrating that AAV vectors can strongly transduce within the latent HSV reservoir in either model. Similarly to HSV, AAV uses fast axonal transport to travel with precision from the epithelia to the ganglia, and thus it is expected that this delivery scheme will sidestep both the neutralization of vector by the humoral immune response as well as the need for high vector doses, both of which are limiting problems for AAV-mediated gene therapy efforts against other conditions.

Efficient delivery of a transgene to the sensory neurons from the periphery involves the preparation of the peripheral tissue surface and delivery of the AAV vector in such a way that gives the AAV vector access to the nerve termini that are present just under the surface of the epithelium, mucosal or ocular surface. The specific preparation is directed by the type of epithelial surface where the vector is to be applied. For mucosal epithelial surfaces (including but not limited to oral, ocular, anal and genital) the surface is mildly abraded or scratched. This can be accomplished, for example, with either with: 1) a sharp needle (bevel-side facing up) in a cross-hatched pattern with a minimum of 3 cross hatches in each direction, or 2) an emery board or other sand-paper-like surface. For mucosal epithelial surfaces this treatment only penetrates several cell layers to expose the nerve termini.

For cornified epithelial surfaces (including but not limited to the skin of the lips, face, buttocks, and non-mucosal genital surfaces), the cornified layers are removed first by abrasion (e.g., with an emery board or sand-paper), and the exposed epithelial surfaces are subsequently scratched or abraded to expose the underlying nerve termini. Following these treatments, the AAV vector is applied and allowed to adsorb for a period of time (e.g., for 20-40 minutes). An alternative method of delivering the AAV vector to the nerve termini is to inject a small volume (0.01-0.05 mL) of the concentrated vector stock intradermally under the skin, mucosal epithelium or cornea (intrastromal inoculation). The vector is then able to enter sensory neurons and mediate its effect.

The following non-limiting embodiments are also provided:

1. A non-naturally occurring fusion protein comprising a TAL binding domain that binds to a target gene of a latent virus and an effector domain, wherein said fusion protein modulates the target gene of the latent virus;

2. The fusion protein of embodiment 1, wherein the TAL binding domain binds to viral polymerase genes, viral genes associated with processing and packaging of viral DNA and/or genes associated the replication of the viral genome;

3. The fusion protein of embodiment 1 or 2, wherein the target gene is an HSV-1 or HSV-2 gene;

4. The fusion protein of embodiment 3, wherein said target gene is selected from ICP27, ICP0, ICP4, UL-5, UL7, UL30 and/or UL25;

5. The fusion protein of embodiments 1-4, wherein said effector domain is a transcription activator, repressor protein, nuclease, endonuclease, topoisomerase, ligase, integrase, recombinase, resolvase, methylase, acetylase, demethylase or deacetylase;

6. The fusion protein of embodiment 5, wherein said effector domain is selected from Mmel, Colicin-E7 (CEA7_ECOLX), EndA, Endo I (END1_ECOLI), Human Endo G (NUCG HUMAN), Bovine Endo G (NUCG_BOVIN), R.HinPI I, l-Basl, I-Bmol, l-Hmul, l-Tev-l, l-Tevll, l-Tevlll, l-Twol, R.Mspl, R.Mval, NucA, NucM, Vvn, Vvn-_CLS, Staphylococcal nuclease (NUC_STAAU), Staphylococcal nuclease (NUC_STAHY), Micrococcal nuclease (NUC_SHIFL), Endonuclease yncB, Endodeoxyribonuclease I (ENRN_BPT7), Metnase, Nb.BsrDI, BsrDI A, Nt.BspD6l (R.BspD6l large subunit), ss.BspD6l (R.BspD6l small subunit), R.PIel, Mlyl, Alwl, Mva1269l, Bsrl, Bsml, Nb.BtsCI, Nt.BtsCI, RlBtsl, R2.Btsl, BbvCI subunit 1, BbvCI subunit 2, BpulOI alpha subunit, BpulOI beta subunit, Bmrl, Bfil, 1-Crel, hExol (EX01JHUMAN), Yeast Exol (EX01_YEAST), *E. coli* Exol, Human TREX2, Mouse TREX1, Human TREX1, Bovine TREX1, Rat TREX1, Human DNA2, Yeast DNA2 (DNA2_YEAST), VP16, RBBP8, p53 or a fragment comprising amino acids 1-42, NFAT, NF-κB, or E1A;

7. A fusion protein of embodiments 1-6, wherein said TAL binding domain comprises:

(SEQ ID NO: 19)
NN-HD-NN-HD-NI-NI-NG-NG-NN-HD-NI-NG-HD-HD-NI-NN-NN;

(SEQ ID NO: 20)
NN-HD-NI-NG-NN-HD-NI-HD-HD-NN-HD-NG-NG-HD-NG-NN-HD;

(SEQ ID NO: 21)
NN-NN-HD-HD-NH-HD-HD-NI-HD-HD-NH-NH-HD-HD-NH-NG-NH-NI-HD-NN;

-continued (SEQ ID N: 22)
HD-NN-HD-HD-NH-HD-NH-HD-HD-HD-NH-HD-HD-NH-NH-HD-HD-HD-NI-NN;

(SEQ ID NO: 23)
NN-NN-NN-NI-HD-NN-HD-NN-HD-NN-NN-HD-HD-NI-NG;

(SEQ ID NO: 24)
NN-NN-HD-NI-NN-NI-NG-NN-NN-HD-NN-HD-NN-NN-NI-NG-NN;

(SEQ ID NO: 25)
NN HD NN HD NI NI NG NG NN HA NI NG HD HD NI NN NN;

(SEQ ID NO: 26)
NN HD NI NG NN HD NI HD HD NN HD NG NG HD NG NN HD;

(SEQ ID NO: 27)
NN NN HD HD NN HD HD NI HD HD NN NN HD HD NN NG NN NI HD NN;

(SEQ ID NO: 28)
HD NN HD HD NN HD NN HD HD HD NN HD HD NN NN HD HD HD NI NN;

(SEQ ID NO: 29)
NN NN NG HD NI NN HD NI NN NN NI NI NN HD HD HD NG NG HD NG;
or (SEQ ID NO: 30)
NN NN HD HD NI NG NN NI NN HD HD NN HD HD NN.

8. A polynucleotide encoding one or more fusion protein of embodiments 1-7;

9. A pharmaceutical composition comprising a fusion protein of embodiments 1-7 and a pharmaceutically acceptable carrier and, optionally an anti-viral agent;

10. The pharmaceutical composition of embodiment 9, wherein said composition comprises an anti-viral agent;

11. A targeted nuclease comprising a guide RNA sequence bound to an endonuclease;

12. The targeted nuclease of embodiment 11, wherein said endonuclease is a bacterial CAS endonuclease;

13. The targeted nuclease of embodiment 11, wherein said endonuclease is a CAS9 endonuclease;

14. The targeted nuclease of embodiment 13, wherein said CAS9 endonuclease is a *Neisseria meningitidis* Cas9 endonuclease;

15. The targeted nuclease of embodiments 11-14, wherein said gRNA sequence targets viral polymerase genes, viral genes associated with processing and packaging of viral DNA and/or genes associated the replication of the viral genome or producing viral RNAs during latency;

16. The targeted nuclease of embodiment 15, wherein the target gene is an HSV-1 or HSV-2 gene;

17. The targeted nuclease of embodiment 16, wherein said target gene is selected from ICP27, ICP0, ICP4, UL-5, UL7, UL30 and/or UL25;

18. The targeted nuclease of embodiment 11, wherein said gRNA sequence is selected from:

ICP4-G1
(SEQ ID NO: 8)
GCGGTGGCCGGCCGCGACGCCACG;

Target (gRNA + PAM)
(SEQ ID NO: 9)
GCGGTGGCCGGCCGCGACGCCACGGGCCGCTT;

```
                          -continued
ICP4-G2
                                             (SEQ ID NO: 10)
GCCGCGGCCGGAGGGACCCGCGGG;

Target (gRNA + PAM)
                                             (SEQ ID NO: 11)
CCCGCGGCCGGAGGGACCCGCGGGCCCCGCTT;

ICP4-G3
                                             (SEQ ID NO: 12)
GGGGGGCCCTGCCGCCGGCGCCGC;

Target (gRNA + PAM)
                                             (SEQ ID NO: 13)
CGGGGGCCCTGCCGCCGGCGCCGCCCGGGATT;

ICP0-G1
                                             (SEQ ID NO: 14)
GGGGTCAGGTACCGCGGGGCGAAC;

Target (gRNA + PAM)
                                             (SEQ ID NO: 15)
AGGGTCAGGTACCGCGGGGCGAACCGCTGATT;

ICP0-G2
                                             (SEQ ID NO: 16)
GGCGTCACGCCCACTATCAGGTAC;

Target (gRNA + PAM)
                                             (SEQ ID NO: 17)
GGCGTCACGCCCACTATCAGGTACACCAGCTT.
```

19. A vector encoding a fusion protein or a targeted nuclease according to any one of embodiments 1-7 or 11-18;

20. The vector of embodiment 19, wherein said vector is an AAV vector;

21. The vector of embodiment 20, wherein said AAV vector comprises a promoter operably linked to a gene encoding a fusion protein or targeted nuclease of embodiments 1-7 or 9-17;

22. The vector of embodiment 21, wherein said promoter is a chicken beta-actin/CMV IE (CBA) promoter;

23. The vector of any one of embodiments 19-22, wherein said promoter comprises the sequence:

```
                                             (SEQ ID NO: 18)
5'tcgaggtgagccccacgttctgcttcactctccccatctcccccccct ccccaccccaatttgtatttatttattttttaattattttgtgcagcg atggggcggggggggggggggcgcgcgccaggcggggcggggcgggg cgaggggcggggcggggcgaggcggagaggtgcggcggcagccaatcaga gcggcgcgctccgaaagtttccttttatggcgaggcggcggcggcggcgg ccctataaaaagcgaagcgcgcggcgggcg3';
```

24. A method of treating a latent viral infection comprising the administration of a vector, fusion protein or targeted nuclease as set forth in any of embodiments 1-7 or 11-23 to a subject having a latent viral infection;

25. The method of embodiment 24, wherein said method comprises the administration of a vector encoding said fusion protein or targeted nuclease to a subject;

26. The method of embodiment 25, wherein said vector is an AAV vector;

27. The method of embodiments 24-25, wherein a fusion protein according to embodiments 1-7 is administered to a subject;

28. The method of embodiment 24, wherein said method comprises the administration of a fusion protein or targeted nuclease as set forth in any of embodiments 1-7 or 11-18 to a subject;

29. The method of embodiment 24, wherein said fusion protein is a TALEN;

30. The method of embodiment 24, wherein said fusion protein is a TALTAD;

31. The method of embodiment 30, wherein said TAL-TAD comprises a TAL binding domain and an effector domain that is a transcription activator;

32. The method of embodiment 31, wherein said transcription activator is VP16;

33. The method of embodiments 31-32, wherein said method further comprises the administration of an anti-viral agent to said subject;

34. The method of embodiment 33, wherein said anti-viral agent is trifluordine, docosanol, acyclovir, ganciclovir, famciclovir, penciclovir, valacyclovir or a combination thereof;

35. The method of any one of embodiments 24-34, wherein said fusion protein or targeted nuclease is administered topically;

36. The method of any of embodiments 24-35, wherein said vector encodes a comprising a TAL binding domain that binds to a target gene selected from viral polymerase genes, viral genes associated with processing and packaging of viral DNA and/or genes associated the replication of the viral genome;

37. The method of embodiment 36, wherein the target gene is an HSV-1 or HSV-2 gene;

38. The method of embodiment 37, wherein said target gene is selected from ICP27, ICP0, ICP4, UL-5, UL7, UL30 and/or UL25;

39. The method of embodiment 36, wherein said TAL binding domain comprises:

```
                                             (SEQ ID NO: 19)
NN-HD-NN-HD-NI-NI-NG-NG-NN-HD-NI-NG-HD-HD-NI-NN-
NN;

(SEQ ID NO: 20)
NN-HD-NI-NG-NN-HD-NI-HD-HD-NN-HD-NG-NG-HD-NG-NN-
HD;

(SEQ ID NO:21)
NN-NN-HD-HD-NH-HD-HD-NI-HD-HD-NH-NH-HD-HD-NH-NG-
NH-NI-HD-NN;

(SEQ ID N: 22)
HD-NN-HD-HD-NH-HD-NH-HD-HD-HD-NH-HD-HD-NH-NH-HD-
HD-HD-NI-NN;

(SEQ ID NO: 23)
NN-NN-NN-NI-HD-NN-HD-NN-HD-NN-NN-HD-HD-NI-NG;

(SEQ ID NO: 24)
NN-NN-HD-NI-NN-NI-NG-NN-NN-HD-NN-HD-NN-NN-NI-NG-
NN;

(SEQ ID NO: 25)
NN HD NN HD NI NI NG NG NN HA NI NG HD HD NI NN
NN;

(SEQ ID NO: 26)
NN HD NI NG NN HD NI HD HD NN HD NG NG HD NG NN
HD;

(SEQ ID NO: 27)
NN NN HD HD NN HD HD NI HD HD NN NN HD HD NN NG
NN NI HD NN;

(SEQ ID NO: 28)
HD NN HD HD NN HD NN HD HD HD NN HD HD NN NN HD
HD HD NI NN;

(SEQ ID NO: 29)
NN NN NG HD NI NN HD NI NN NN NI NI NN HD HD HD
NG NG HD NG;
or
                                             (SEQ ID NO: 30)
NN NN HD HD NI NG NN NI NN HD HD NN HD HD NN.
```

40. The method of embodiment 24, wherein said vector encodes a targeted nuclease that targets viral polymerase genes, viral genes associated with processing and packaging of viral DNA and/or genes associated the replication of the viral genome;

41. The method of embodiment 40, wherein said target gene is an HSV-1 or HSV-2 gene;

42. The method of embodiment 41, wherein said target gene is selected from ICP27, ICP0, ICP4, UL-5, UL7, UL30 and/or UL25;

43. The method of embodiment 42, wherein said gRNA sequence is selected from:

```
ICP4-G1
                                      (SEQ ID NO: 8)
GCGGTGGCCGGCCGCGACGCCACG;

Target (gRNA + PAM)
                                      (SEQ ID NO: 9)
GCGGTGGCCGGCCGCGACGCCACGGGCCGCTT;

ICP4-G2
                                     (SEQ ID NO: 10)
GCCGCGGCCGGAGGGACCCGCGGG;

Target (gRNA + PAM)
                                     (SEQ ID NO: 11)
CCCGCGGCCGGAGGGACCCGCGGGCCCCGCTT;

ICP4-G3
                                     (SEQ ID NO: 12)
GGGGGGCCCTGCCGCCGGCGCCGC;

Target (gRNA + PAM)
                                     (SEQ ID NO: 13)
CGGGGGCCCTGCCGCCGGCGCCGCCCGGGATT;

ICP0-G1
                                     (SEQ ID NO: 14)
GGGGTCAGGTACCGCGGGGCGAAC;

Target (gRNA + PAM)
                                     (SEQ ID NO: 15)
AGGGTCAGGTACCGCGGGGCGAACCGCTGATT;

ICP0-G2
                                     (SEQ ID NO: 16)
GGCGTCACGCCCACTATCAGGTAC;

Target (gRNA + PAM)
                                     (SEQ ID NO: 17)
GGCGTCACGCCCACTATCAGGTACACCAGCTT.
```

All patents, patent applications, provisional applications, and publications referred to or cited herein are incorporated by reference in their entirety, including all figures and tables, to the extent they are not inconsistent with the explicit teachings of this specification. Following are examples which illustrate procedures for practicing the invention. These examples should not be construed as limiting. All percentages are by weight and all solvent mixture proportions are by volume unless otherwise noted.

Example 1

TALEN/TALTAD Activity

Our initial validation experiments have focused on cell culture models of HSV-1 infection. To demonstrate that the TALENs are active in live cells, we generated indicator constructs containing the HSV-1 target sites embedded between a fragment of the HIV-1 rev gene and the green fluorescent protein (gfp) gene. The HSV-1 fragment is inserted in frame such that gfp is properly translated from the construct, but such that cleavage should disrupt gfp expression by either destabilizing the indicator plasmid or by generating a frame-shift mutation. As shown in FIG. 2B, a control TALEN targeting a control, cellular DNA target indeed blocks gfp expression from the cognate indicator plasmid but not the HSV-1-based indicator. Conversely, an ICP0-specific TALEN blocks gfp expression if the vector contains the relevant HSV-1 target but does not affect the control indicator.

To extend these data, we also measure expression of the Rev-GFP protein by Western blot analysis. As shown in FIG. 2C, the HSV-1 miR-H1/H6-specific TALEN strongly and specifically inhibits expression of a Rev-GFP fusion bearing the miR-H1/H6 DNA target, whereas both ICP0-specific TALENs specifically block expression of Rev-GFP fusion proteins bearing the cognate HSV-1 derived ICP0 DNA target. Therefore, it is shown that the TALENs are able to specifically cleave and inactivate episomal DNA molecules in living cells, but only if these DNA plasmids contain the relevant DNA target.

Figures 3A, 3B:
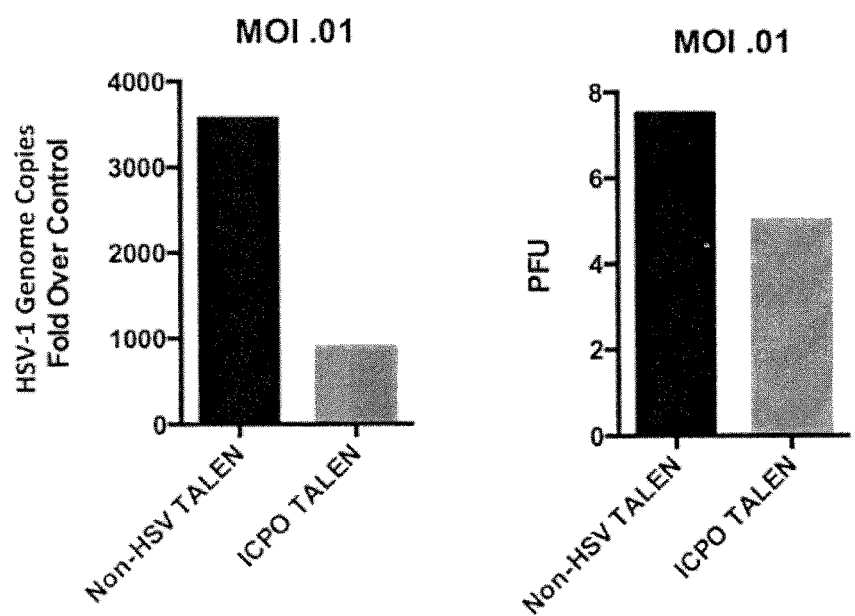
FIGS. 3A-3B. Effect of ICP0-specific TALENs on lytic HSV-1 replication. A) Measurement of HSV-1 DNA copy number, as determined by qPCR, in the presence or absence of an ICP0-specific TALEN pair. B) Similar to panel A, but measuring virus progeny production.

We also investigated the ability of ICP0-specific TALENs to inhibit lytic HSV-1 replication in cell culture. 293T cells were transfected with one of the ICP0-specific TALEN pairs and the cells were then infected with 0.01 pfu per cell of HSV-1. Transfection efficiency was ≈80%, and we noted a close to 80% inhibition in HSV-1 DNA replication in the transfected cells, with an accompanying significant drop in virus replication (FIG. 3). As lytically replicating HSV-1 shuts down host cell gene expression, which includes TALEN expression, attaining this level of inhibition is very promising.

Figure 4:
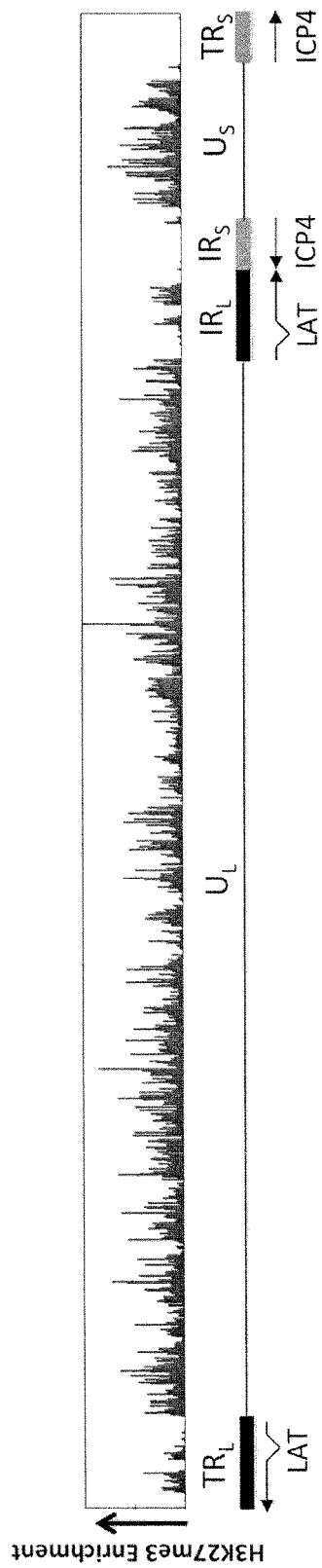
FIG. 4. ChIP-seq analysis for the heterochromatin mark H3K27triMe on the HSV-1 latent genome. Sheared chromatin from mice latently infected with either 17+ (wt) or 17ΔPst (LAT null mutant) was immunoprecipitated with antibody against H3K27triMe. The isolated DNA was enriched for HSV-1 sequences using a custom enrichment bead array (Agilent SureSelect) and a library constructed and amplified for Illumina sequencing. These analyses reveal significant regions that are under-enriched in heterochromatin during latency. These include the promoter and 5' region of the LAT, as well as a large portion of the ICP4 CDS.

While our initial TALEN constructs certainly demonstrate proof-of-concept that these can effectively target the HSV genome in vitro, latent genomes in vivo are packaged into nucleosomes, much of which becomes associated with heterochromatin. As other DNA-binding proteins are less effective in acting on heterochromatized template compared to euchromatized template, we expect TALENs to exhibit greater activity on regions of viral DNA associated with lower levels of heterochromatic histone marks. To this end we have successfully profiled latent HSV-1 genomes from sensory ganglia of infected mice and identified key lytic gene regions that are significantly under-enriched in the heterochromatin mark trimethylated H3K27 (H3K27me3). A few such regions occur in the coding region of the major transactivator ICP4 (FIG. 4), and we have chosen targets within these sites in designing our ICP4-targeted TALENs under the expectation that these regions will be more accessible for more efficient cleavage by targeted endonucleases. Furthermore, these euchromatic regions include sub-stretches of DNA that have been shown to, upon mutation, produce phenotypically modified forms of ICP4 with impaired activity. One such mutation results in an ICP4 protein that retains the ability to dimerize with other ICP4 proteins and to bind to viral DNA, but loses the ability to transactivate. By targeting one TALEN pair to this region, we anticipate that mutagenized genomes may produce dominant negative forms of ICP4, impairing reactivation even from non-mutagenized genomes.

Figure 5A:
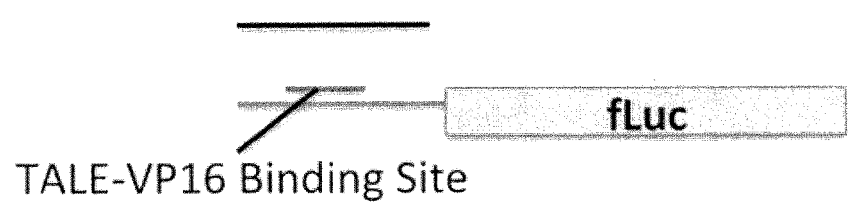
FIGS. 5A-5B. Specific activation of the ICP0 or ICP4 promoter by TALE-VP16 fusions. Indicator constructs were generated that place either the HSV-1 ICP0 or ICP4 promoter 5' to the Firefly luciferase (Fluc) indicator gene and these were then co-transfected into 293T cells with ICP0-TALE-VP16 or ICP4-TALE-VP16 fusion protein expression plasmids. At 24 hours, Fluc activity was determined and normalized to an internal control plasmid encoding *Renilla* luciferase.
Figure 5B:
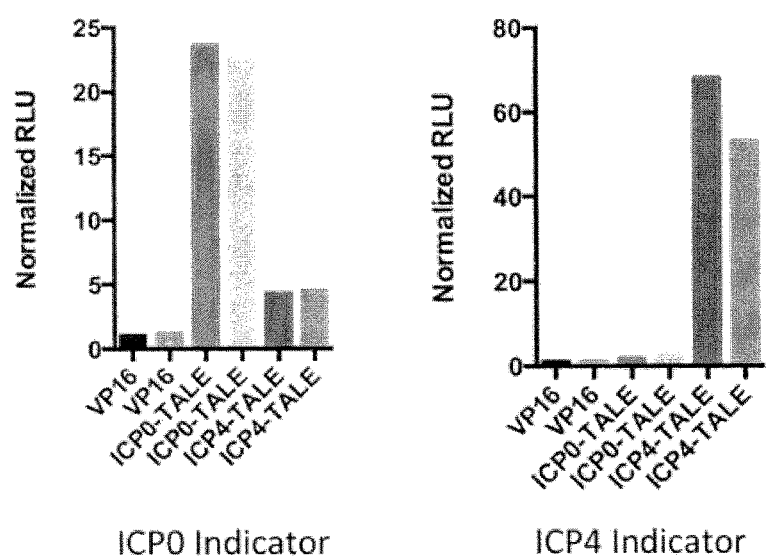

To confirm that the TALE-VP16 fusions are functional, we generated indicator constructs bearing either the HSV-1 ICP0 promoter or the HSV-1 ICP4 promoter linked to the firefly luciferase (Fluc) indicator gene, and then co-transfected these indicators in duplicate with either the ICP0-specific or ICP4-specific TALE-VP16, or alternatively VP16 without fusion to a TAL effector. As shown in FIG. 5, we observed ≈20-fold activation of the ICP0 promoter by the cognate ICP0-specific TALE-VP16 fusion and ≈60 fold activation of the ICP4 promoter by the cognate ICP4-specific TALE-VP16 fusion. Control vectors gave no activation. Therefore, these TALE-VP16 fusions are fully able to specifically activate their cognate viral promoters in living cells.

Example 2

CRISPR/Cas Systems are Effective Against Viral Episomes

To demonstrate that CRISPR/Cas systems can be effective against viral DNA episomes we employed the prototypic *Streptococcus Pyogenes* Cas9. SPCas9 cleavage is highly specific and comparable to that shown earlier with TALENs in FIG. 2, and retargeting involves using a distinct gRNA. When the SPCas9 RGNs are targeted to replicating episomes in culture, we observe their complete elimination from cells.

Figure 6A:
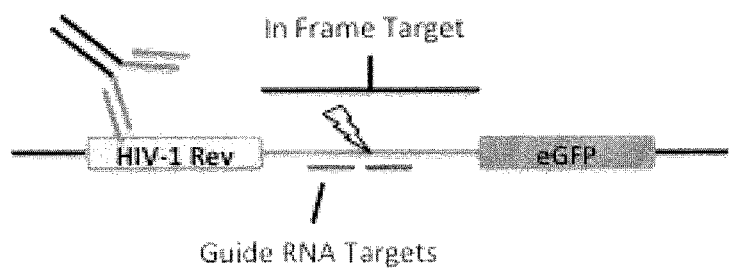
FIGS. 6A-6B. RGN cleavage results in episome elimination from culture. Panel (A) shows a schematic of the reporter system employed. (B) A Western blot cross talk experiment comparing an HSV-1 ICP0 specific guide RNA to an HBV reverse transcriptase specific guide RNA. An anti-FLAG antibody demonstrates SPCas9 expression, and the anti-Rev antibody demonstrates highly specific elimination of the replicating episomal DNA reporter.
Figure 6B:
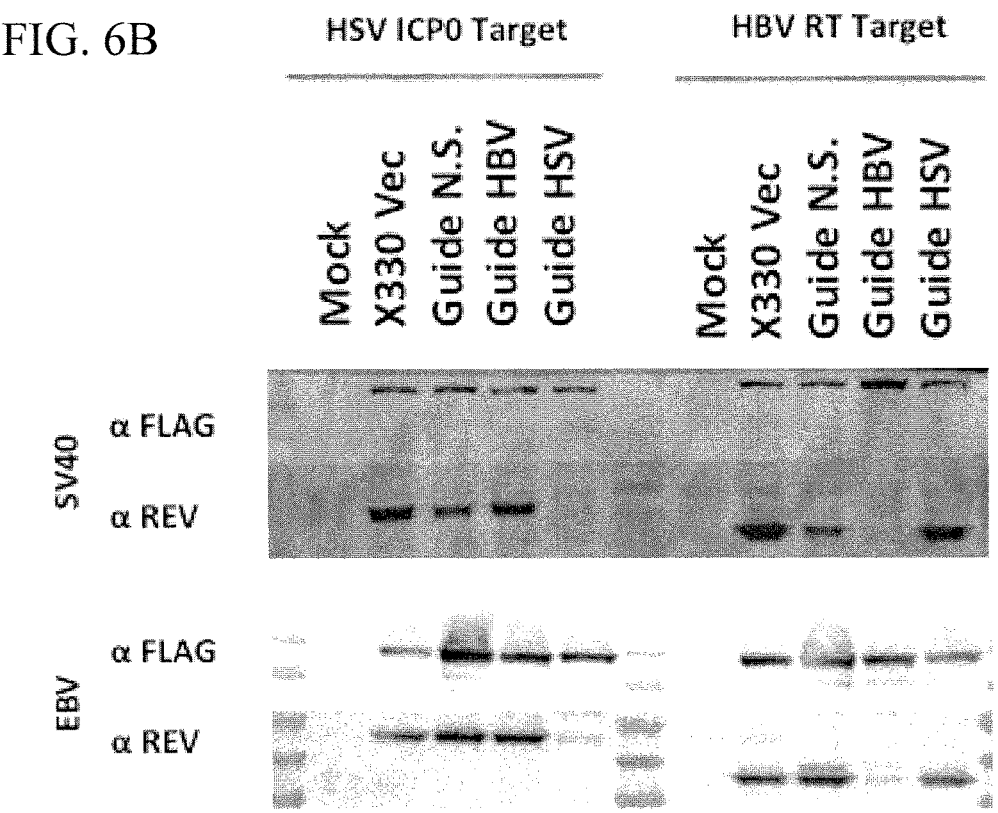

In FIG. 6, we have targeted viral DNA encoding the essential HSV-1 ICP0 protein or the Hepatitis B virus (HBV) reverse transcriptase, with SPCas9 using the reporter assay detailed in FIG. 2. In contrast to the expected reduction in GFP expression predicted by the rate of mutagenesis induce by non-homologous end joining, we observed a binary result interpretable as elimination of the episome from culture. This was the case for DNA episomes based on either an SV40 or Epstein-Barr virus (EBV) derived viral origin of replication, as shown again by Western blot using an antibody specific of Rev (FIG. 6B). This episome elimination phenomenon is highly novel and very advantageous, and HSV-1-specific gRNAs can be combined to target multiple viral genes simultaneously, thus enhancing the desired inhibitory effect.

The inhibitory effect of the observed fragmentation of circular viral DNA episomes is potentially further enhanced by the high likelihood of simultaneous mutagenesis of essential viral genes resulting from error prone dsDNA break repair. Because a single Cas9 protein can bind to several specific DNA targets, depending on the presence of appropriate gRNAs, one could also potentially cleave the HSV-1 genome at two or more places simultaneously to generate lethal viral deletion mutants. Moreover, the CRISPR/Cas system uses endonucleases that are active as single polypeptides, rather than as heterodimeric proteins as for the TALENs. As a result, sequences encoding a single Cas9 protein and one or more gRNA cassettes can be packaged into a viral vector, such as an Adeno associated virus (AAV) based vector or a vector based on an attenuated HSV-1 derivative, and subsequently used to transduce cells in vivo leading to the cleavage of one or several specific viral DNA targets in these cells, depending on the identity on the guide RNAs co-expressed by the vector.

The SPCas9 gene is too large to package in an AAV vector, so we have selected Type II CRISPR/Cas9 system from *Neisseria meningitidis* (NMCas9; SEQ ID NO: 1), which is a minimal but complete RNA guided nuclease (RGN), for more intensive analysis in the context of AAV-based vectors. This highly specific and effective dsDNA endonuclease can be employed to destroy HSV-1 episomes and/or mutationally inactivate HSV-1 open reading frames both in culture and in vivo, initially in mice but later potentially in human patients.

Figure 8:
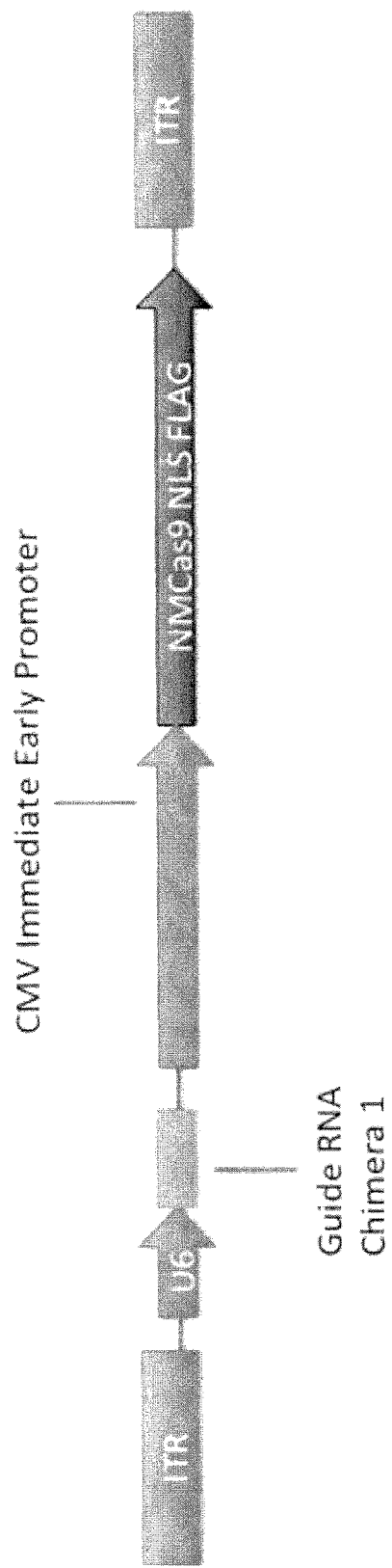
FIG. 8. AAV NMCas9 vector design. Schematic representation of an AAV-based vector designed to express NMCas9; the NMCas9 protein expression cassette uses the strong CMV immediate early promoter and is flanked 3' by a genomic poly(A) addition site. The U6 Pol III promoter is used to drive gRNA expression. ITR: Inverted Terminal Repeat.
Figure 9A:
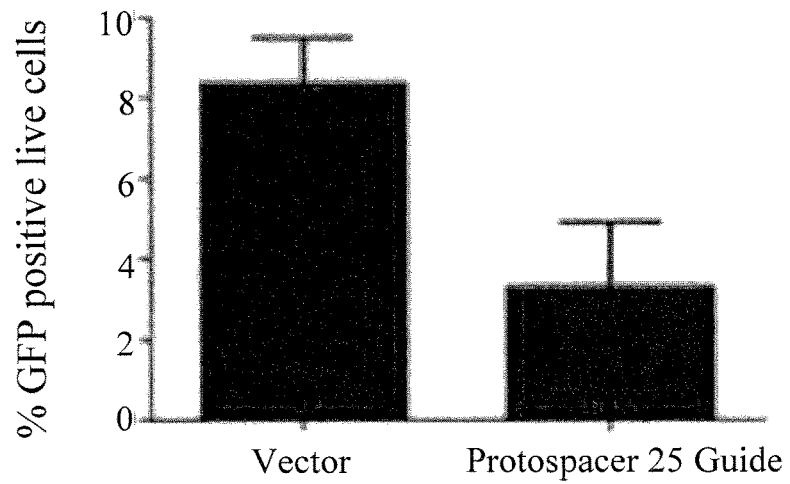
FIGS. 9A-9E. NMCas9-specific gRNAs substantially reduce the frequency of GFP positive cells as shown by FACS. Cells were co-transfected with the Rev-target-eGFP reporter construct depicted in FIG. 7B with a gRNA specific target. Shown in A is a positive control gRNA, in B and C are candidate gRNAs targeting HSV-1 ICP0 and ICP4, showing efficient knockdown of eGFP expression. This assay is quantitative and ideal to screen gRNAs for cleavage efficiency. In panels D and E, Western analysis is used to demonstrate NMCas9 expression by FLAG Western (upper panel) as well as gRNA-specific reductions in the expression level of the episome derived Rev:GFP fusion protein (lower panel), which reflects a reduction in the level of the targeted viral episome. The gRNAs used in panel D are bacterial gRNAs that act here as positive controls.
Figure 9B:
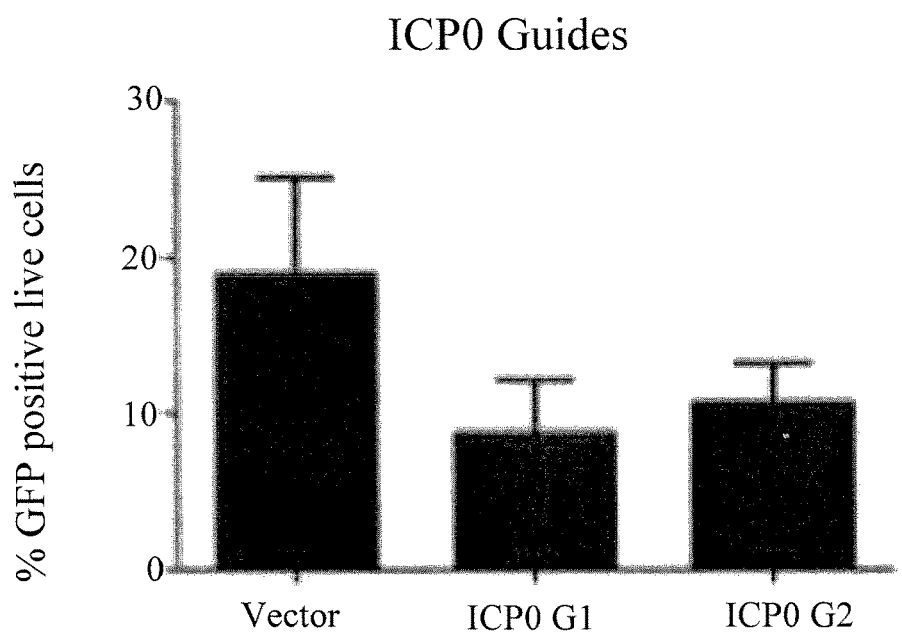
Figure 9C:
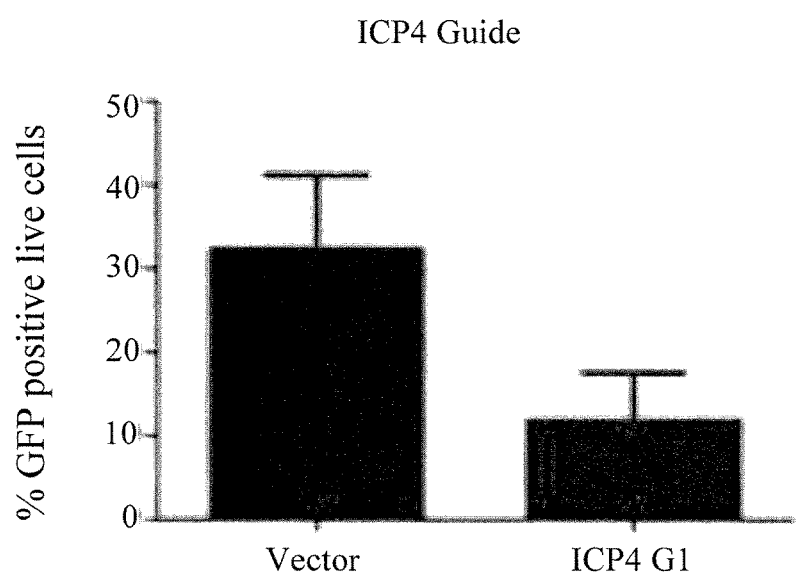
Figures 9D, 9E:
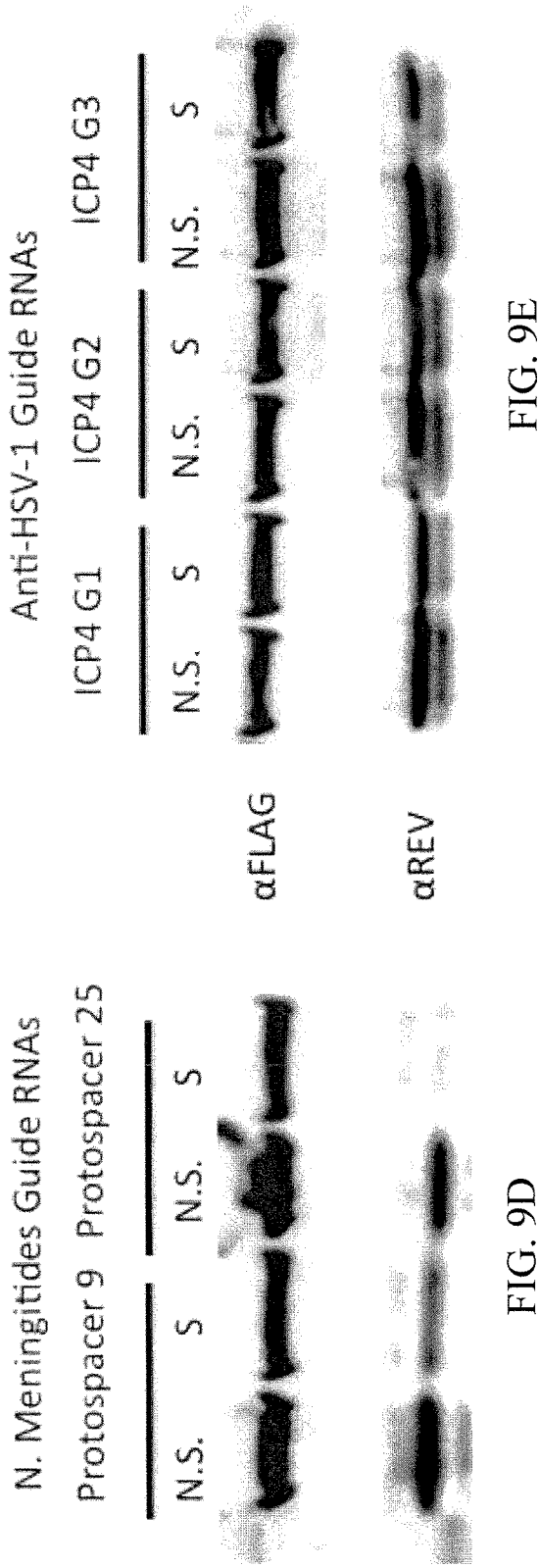

To further minimize total RGN size for AAV packaging, we have optimized the NMCas9 nuclease and the gRNA expression cassettes by using small but effective promoters (FIG. 8). Published work with SPCas9 describes a fusion of the two *S. pyogenes* small RNAs that are essential for SPCas9 function, the crRNA and tracrRNA, into a single functional guide RNA "chimera". Guide RNA chimeras consist of two essential portions; a 5' portion that is completely complementary to the sequence of the target DNA and a conserved structured 3' terminus essential for Cas9 protein binding. We have extended this work by developing and characterizing a gRNA chimera that fuses a portion of the *N. meningitidis* crRNA and tracrRNA. This minimal gRNA can be readily modified to target any DNA locus by altering the sequence overlined in FIG. 7A, and is expressed from a minimal RNA polymerase III (Pol III) based cassette. This gRNA is functional when loaded into NMCas9, as demonstrated by the GFP-based reporter assay, similar to the assay for TALEN activity (FIG. 2A), that is described in FIG. 6A. Expression of the NMCas9 protein together with an appropriate guide RNA results in loss of GFP expression as detected by microscopy (FIG. 7C), and loss of Rev-fusion protein expression, as detected by Western blot using an antibody specific for Rev (FIG. 7B). This assay demonstrates that we have successfully expressed adequate NMCas9 and gRNA levels in culture, and that DNA target cleavage is both highly efficient and specific. Furthermore, this result mirrors the work shown in FIG. 6 using SPCas9 and demonstrates that the smaller NMCas9 protein is also capable of inducing the endonucleolytic destruction of DNA episomes in culture. Control targets from N. *Meningitides* were then compared to synthetic guides we designed to target the HSV-1 ICP0 and ICP4 genes and we have clearly shown that in culture NMCas9 is effective against HSV-1 targets as measured by quantitative FACs assay (FIG. 9, panels A-C) and by disappearance of the rev-fusion protein (FIG. 9, panels D and E).

To facilitate delivery of the NMCas9 payload to cells in vivo, we have designed and constructed the AAV vector that is schematically represented in FIG. 8. The human CMV immediate early promoter drives NMCas9 expression at the 3' end of the vector. 5' of this protein expression cassette we have placed a Pol III-driven gRNA expression cassette, to avoid the transcriptional interference known to result from Pol II promoters located 5' to Pol III promoters. For our initial analysis of effectiveness in vivo, we have selected several DNA targets in the HSV-1 LAT region, which is the sole transcribed region during neuronal latency, as well as in the essential viral ICP4 gene (FIG. 1). AAV vectors encoding HSV-1-specific NMCas9-based payloads will be directly compared with non-specific control AAV vectors. Importantly, trigeminal ganglia tissue can be readily quantitatively evaluated for loss of HSV-1 episomes by quantitative PCR and loss of reactivateable HSV-1 can also be measured by neuronal explanation. NMCas9 delivered by AAV represents a novel, and potentially highly effective, mode of elimination of HSV-1 from infected neuronal tissues in vivo.

Example 3

ICP4 Targeted TALEN Activity

"CTRL TALEN", assembled using the Joung Lab Real Assembly TALEN kit, contains an RVD-array targeted to CMV sequences not present in the virus or cell genomes. The "RA-TALEN ICP0" pair, assembled using the Joung Lab Real Assembly TALEN kit, contain RVD arrays targeted to the first exon of the ICP0 protein (see 'X' in ICP0 gene, FIG. 10). RVD compositions are:

RA-TALEN ICP0 (left):
(SEQ ID NO: 25)
NN HD NN HD NI NI NG NG NN HA NI NG HD HD NI NN NN;

RA-TALEN ICP0 (right):
(SEQ ID NO: 26)
NN HD NI NG NN HD NI HD HD NN HD NG NG HD NG NN HD.

Figure 10:
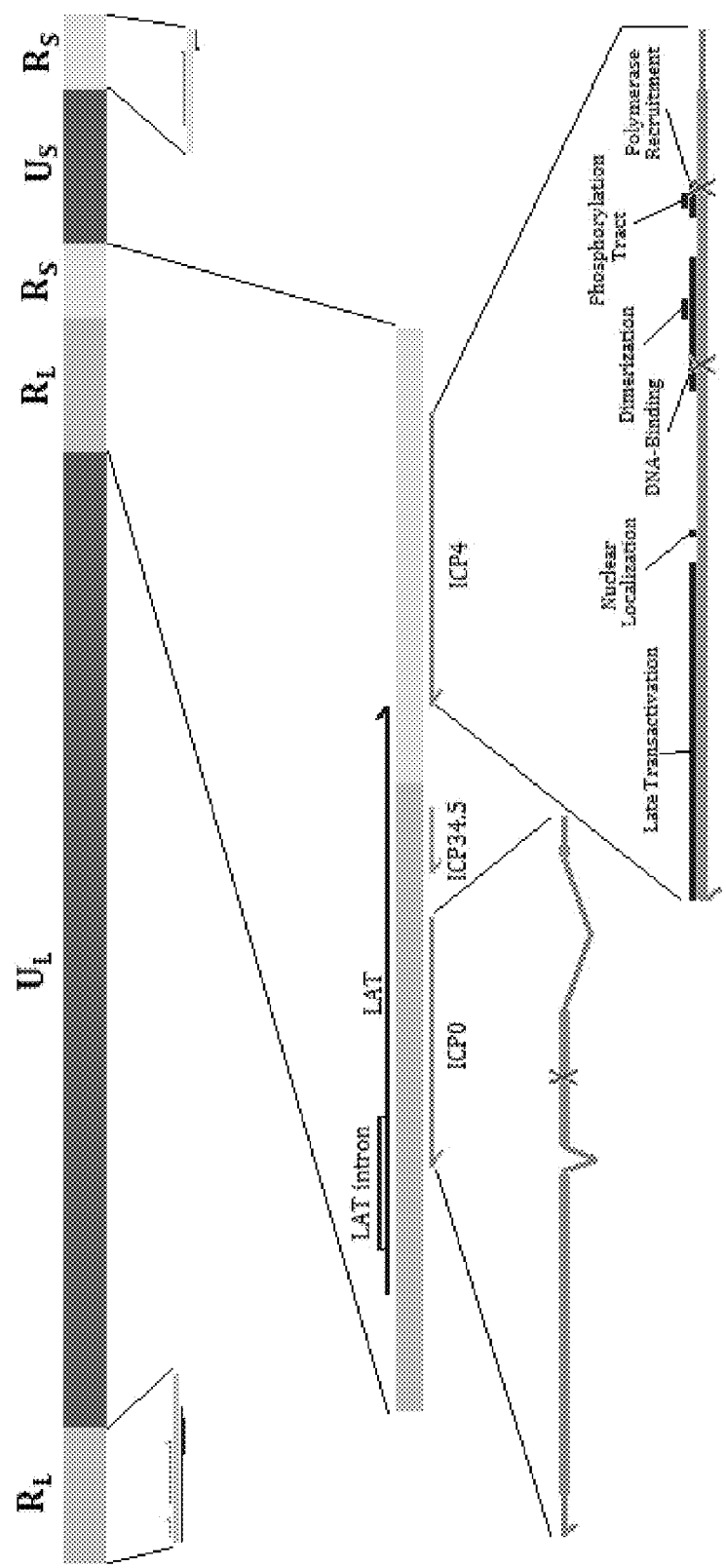
FIG. 10. Map of the HSV-1 Genome with TALEN Targets Marked. HSV-1 repeat regions are shown enlarged, including maps of targeted HSV-1 proteins. Characterized functional domains of ICP4 are labeled. Targets of TALENs are marked by a red 'X'.
Figure 11:
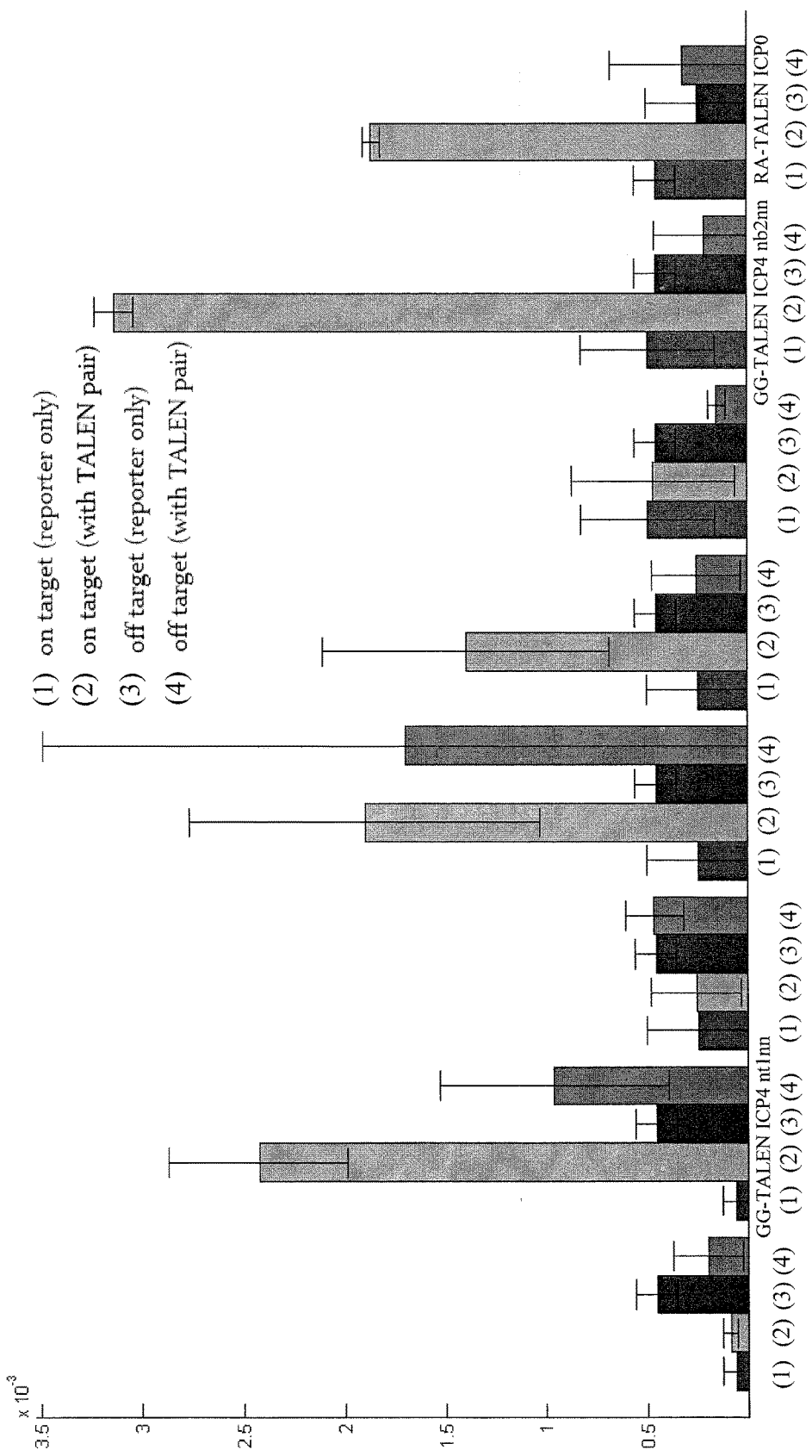
FIG. 11. Specificity of TALEN target pairs. In cases where the sequence in the firefly luciferase gene is recognized by the TALEN pair in a given reaction (column identified as "2") for each TALEN pair, successful cleavage and subsequent repair of the firefly luciferase gene results in increased relative luciferase signal (y-axis, arbitrary units) compared to wells transfected with a given reporter alone (column identified as "1") for each TALEN pair. Each ICP4-targeted TALEN pair was also mixed in a reaction containing an ICP0 target in the firefly luciferase gene to assay for off-target amplification of luciferase (column identified as "4") for each TALEN pair compared to background levels of the ICP0 target reporter (column identified as "3") for each TALEN pair. TALEN pairs used in subsequent assays are labeled; other data sets are for ICP4-targeted TALEN pairs with alternative RVD composition.

The GG-TALEN ICP4_nt1nn pair, assembled using the Voytas Lab Golden Gate Assembly TALEN kit and Yamamoto Lab TALEN Accessory Pack (acquired via Addgene), contain RVD arrays targeted to a coding region of the ICP4 protein corresponding to a functional domain essential for ICP4's ability to transactivate other HSV genes (see right 'X' in ICP4 gene, FIG. 10). RVD compositions are:

GG-TALEN ICP4_nt1nn (left):
(SEQ ID NO: 27)
NN NN HD HD NN HD HD NI HD HD NN NN HD HD NN NG NN NI HD NN;

GG-TALEN ICP4_nt1nn (right):
(SEQ ID NO: 28)
HD NN HD HD NN HD NN HD HD HD NN HD HD NN NN HD HD HD NI NN.

The GG-TALEN ICP4_nb2nn pair, assembled using the Voytas Lab Golden Gate Assembly TALEN kit and Yamamoto Lab TALEN Accessory Pack (acquired via Addgene), contain RVD arrays targeted to a coding region of the ICP4 protein corresponding to a functional domain essential for ICP4's DNA-binding ability (see left 'X' in ICP4 gene, FIG. 10).

GG-TALEN ICP4_nb2nn (left):
(SEQ ID NO: 29)
NN NN NG HD NI NN HD NI NN NN NI NI NN HD HD HD NG NG HD NG;

GG-TALEN ICP4_nb2nn (right):
(SEQ ID NO: 30)
NN NN HD HD NI NG NN NI NN HD HD NN HD HD NN.

Cleavage Efficiency of a Panel of ICP4-targeted TALENs. 293T cells were seeded in triplicate into a 96-well plate containing a transfection solution composed of Lipofectamine 2000 and a mixture of plasmid DNA composed of a pair of TALEN expression vectors, a reporter containing a TALEN target sequence inserted into the firefly luciferase gene, and a reporter containing the *renilla* luciferase gene (to allow for normalization between wells with respect to transfection efficiency). 24 hours after transfection, luciferase signal was assayed using the Promega Dual-Glo Luciferase Assay System according to the manufacturer's protocol. In cases where the sequence in the firefly luciferase gene is recognized by the TALEN pair in a given reaction (column identified as "2") for each TALEN pair, successful cleavage and subsequent repair of the firefly luciferase gene results in increased relative luciferase signal (y-axis, arbitrary units) compared to wells transfected with a given reporter alone (column identified as "1") for each TALEN pair. Each ICP4-targeted TALEN pair was also mixed in a reaction containing an ICP0 target in the firefly luciferase gene to assay for off-target amplification of luciferase (column identified as "4") for each TALEN pair compared to background levels of the ICP0 target reporter (column identified as "3") for each TALEN pair. TALEN pairs used in subsequent assays are labeled; other data sets are for ICP4-targeted TALEN pairs with alternative RVD composition.

Figure 12:
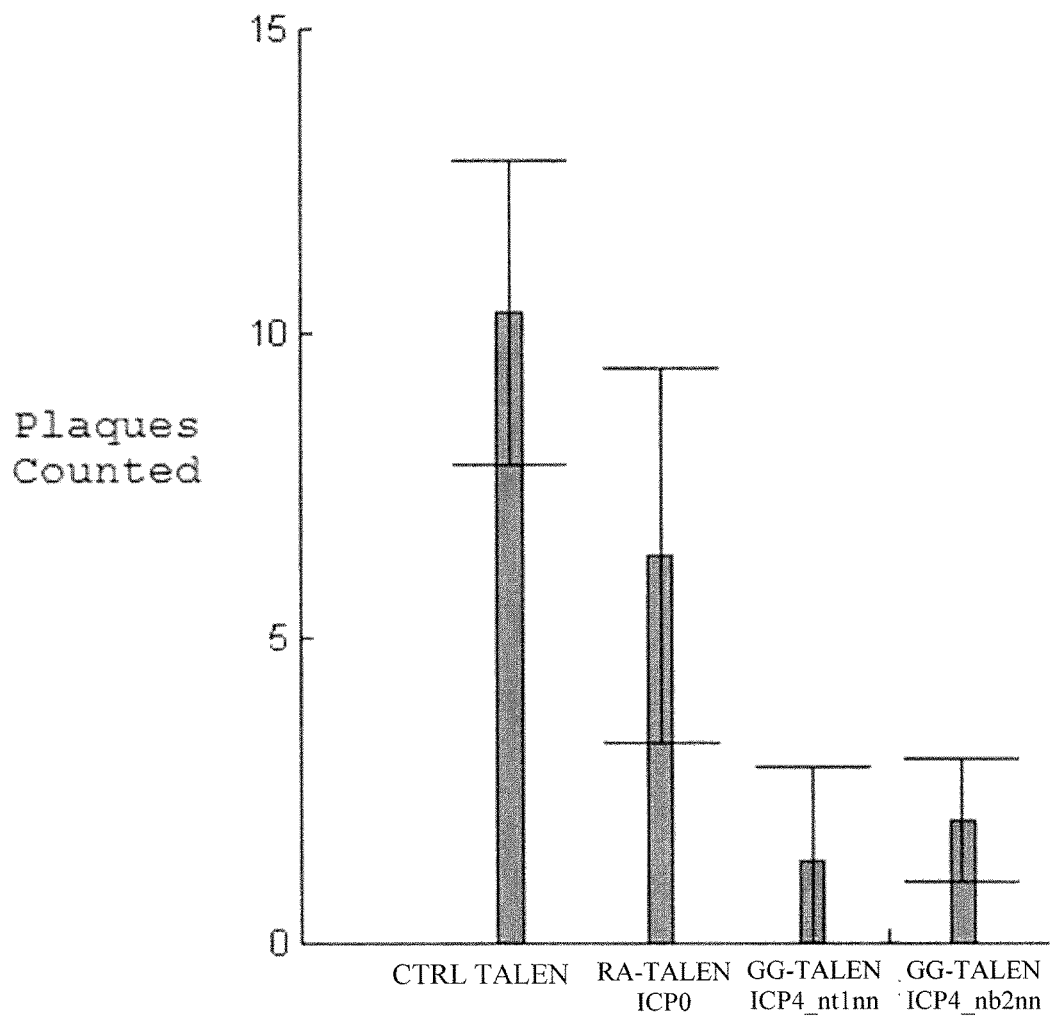
FIG. 12. Antiviral Action of HSV1-targeted TALENs. Fluorescence microscopy 24 hours after transfection revealed a lower estimate of near 30% transfection efficiency. 48 hours after transfection, cells were infected with HSV-1 strain 17syn+ at an MOI of 1.12 hours after infection, cells and medium were harvested from each well, subjected to two freeze/thaw cycles, and concentration of infectious virus was determined via plaque assay. Numbers of plaques for each triplicate are shown. Relative to control wells, cells containing either GG-TALEN pair produced substantially fewer infectious virions.

Antiviral Action of HSV1-Targeted TALENs. 293T cells seeded into a 24-well plate were transfected in triplicate using a plasmid mixture containing ~233 ng left-binding TALEN expression vector, ~233 ng right-binding TALEN expression vector, and about ~33 ng pIRES-EGFP-puro (enabling visualization of transfection efficiency and puromycin selection of transfected cells) via the TransIT-293 transfection reagent according to the manufacturer's protocol. Fluorescence microscopy 24 hours after transfection revealed a lower estimate of near 30% transfection efficiency. 48 hours after transfection, cells were infected with HSV-1 strain 17syn+ at an MOI of 1.12 hours after infection, cells and medium were harvested from each well, subjected to two freeze/thaw cycles, and concentration of shown (see FIG. 12). Relative to control wells, cells containing either GG-TALEN pair produced substantially fewer infectious virions. The individual TALEN pairs are described above.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

We claim:

1. A method of treating a latent viral infection comprising the administration of a fusion protein comprising a TAL binding domain that binds a target gene of a latent virus and an effector domain to a subject having a latent viral infection, wherein (a) the target gene is selected from ICP27, ICP0, ICP4, UL5, UL7, UL30, LAT and/or UL25, (b) the effector domain is an endonuclease, and (c) the fusion protein modulates the target gene of the latent virus, wherein the viral infection is caused by an HSV-1 or HSV-2 virus.

2. A method of treating a latent viral infection comprising the administration of a vector encoding the fusion protein according to claim 1 to a subject having a latent viral infection.

3. The method of claim 1, wherein the target gene is ICP4 and the effector domain is Mme1.

* * * * *